US009205131B2

(12) United States Patent  
Bui

(10) Patent No.: US 9,205,131 B2
(45) Date of Patent: Dec. 8, 2015

(54) USE OF IL-17D FOR THE TREATMENT AND PREVENTION OF CANCERS

(75) Inventor: Jack Bui, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 6 days.

(21) Appl. No.: 14/004,421

(22) PCT Filed: Mar. 30, 2012

(86) PCT No.: PCT/US2012/031407
§ 371 (c)(1),
(2), (4) Date: Nov. 22, 2013

(87) PCT Pub. No.: WO2012/135598
PCT Pub. Date: Oct. 4, 2012

(65) Prior Publication Data
US 2014/0086868 A1    Mar. 27, 2014

Related U.S. Application Data

(60) Provisional application No. 61/469,531, filed on Mar. 30, 2011.

(51) Int. Cl.
*A61K 38/20*    (2006.01)
(52) U.S. Cl.
CPC ...................................... *A61K 38/20* (2013.01)
(58) Field of Classification Search
None
See application file for complete search history.

(56) References Cited

U.S. PATENT DOCUMENTS

| 5,595,756 | A * | 1/1997 | Bally et al. ................ 424/450 |
| 2004/0219094 | A1* | 11/2004 | Motchenbacher et al. .......... 423/594.17 |
| 2004/0219096 | A1* | 11/2004 | De Waal Malefyt et al. ............ 424/1.41 |
| 2005/0186664 | A1* | 8/2005 | Rosen et al. ................ 435/69.7 |
| 2010/0233081 | A1* | 9/2010 | Warren et al. ............... 424/1.61 |

OTHER PUBLICATIONS

IL-17D printout (NCBI Gene Database; downloaded from http://www.ncbi.nlm.nih.gov/gene/53342 on May 19, 2014).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Sporn et al, "Chemoprevention of Cancer," Carcinogenesis, vol. 21 (2000), 525-530.*
Gura T (Science, 1997, 278(5340): 1041-1042, encloses 1-5).*
Jain RK (Scientific American, Jul. 1994,58-65).*
Auerbach et al (Cancer and Metastasis Reviews, 2000, 19: 167-172).*
NP_612141.1 downloaded from http://www.ncbi.nlm.nih.gov/protein/NP_612141.1 on Oct. 18, 2014.*
Gene ID 53342 updated on Oct. 10, 2014, downloaded from http://www.ncbi.nlm.nih.gov/gene/53342 on Oct. 18, 2014.*
Bui, J.D., Uppaluri, R., Hsieh, C.S. and Schreiber, R.D. Comparative analysis of regulatory and effector T cells in progressively growing versus rejecting tumors of similar origins. *Cancer Res* 66, 7301-7309 (2006).
Dunn, G.P., Bruce, A. T., Ikeda, H., Old, L. J. and Schreiber, R.D. Cancer immunoediting: from immunosurveillance to tumor escape. *Nature Immunol.* 3, 991-998 (2002).
Dupage M.et al. Expression of tumor-specific antigens underlies cancer immunoediting. *Nature* 482, 405-409 (2012).
Flood, P.M., Schreiber, H. and Ron, Y. Protective immunity to progressive tumors can be induced by antigen presented on regressor tumors. *J Immunol* 138, 3573-3579 (1987).
Fridlender ZG. et al. Polarization of tumor-associated neutrophil phenotype by TGF-beta:"N1" versus "N2" TAN. *Cancer Cell* 16(3), 173-174 (2009).
Koebel, C. M. et al. Adaptive immunity maintains occult cancer in an equilibrium state. *Nature* 450, 903-907 (2007).
Matsushita H.et al. Cancer exome analysis reveals a T-cell-dependent mechanism of cancer immunoediting. *Nature* 482, 400-404 (2012).
O'Sullivan, T., Saddawi-Konefka, R., Gross, E., Tran, M., Mayfield, S., Ikeda, H. and Bui, J.D. Interleukin-17D Mediates Tumor Rejection through Recruitment of Natural Killer Cells. *Cell Reports* 7, 989-998 (2014).
PCT International Preliminary Report on Patentability dated Oct. 1, 2013 2012 issued in International Patent Application No. PCT/US2012/031407.
PCT International Search Report and Written Opinion dated Jun. 22, 2012 issued in International Patent Application No. PCT/US2012/031407.
Pelletier M., Bouchard A. and Girard D. In vivo and in vitro roles of IL-21 in inflammation. *J Immunol* 173, 7521-7530 (2004).
Schreiber, R. D., Old, L. J. and Smyth, M. J. Cancer immunoediting: integrating immunity's roles in cancer suppression and promotion. *Science* 331, 1565-1570 (2011).
Shankaran, V.et al. IFNc and lymphocytes prevent primary tumor development and shape tumor immunogenicity. *Nature* 410, 1107-1111 (2001).
Starnes, T., Broxmeyer, H.E., Robertson, M.J.and Hromas, R. Cutting edge: IL-17D, a novel member of the IL-17 family, stimulates cytokine production and inhibits hemopoiesis. *J Immunol* 169, 642-646 (2002).
Vesely, M.D., Kershaw, M. H., Schreiber, R. D.and Smyth, M. J. Natural innate and adaptive immunity to cancer. *Annu.Rev.Immunol.* 29, 235-271 (2011).
Zou W. and Chen L. Inhibitory B7-family molecules in the tumor microenvironment. *Nature Reviews Immunology* 8, 467-477 (2008).

* cited by examiner

*Primary Examiner* — Brian J Gangle
*Assistant Examiner* — Andrea McCollum
(74) *Attorney, Agent, or Firm* — Weaver Austin Villeneuve & Sampson LLP

(57) ABSTRACT

The present invention relates to the treatment and prevention of cancers, particularly cancers whose growth is reduced or inhibited by immunostimulatory therapy, by the administration of interleukin-17D (IL-17D), compounds that can increase the production, half-life, or activity of IL-17D, or compositions that contain IL-17D.

12 Claims, 12 Drawing Sheets

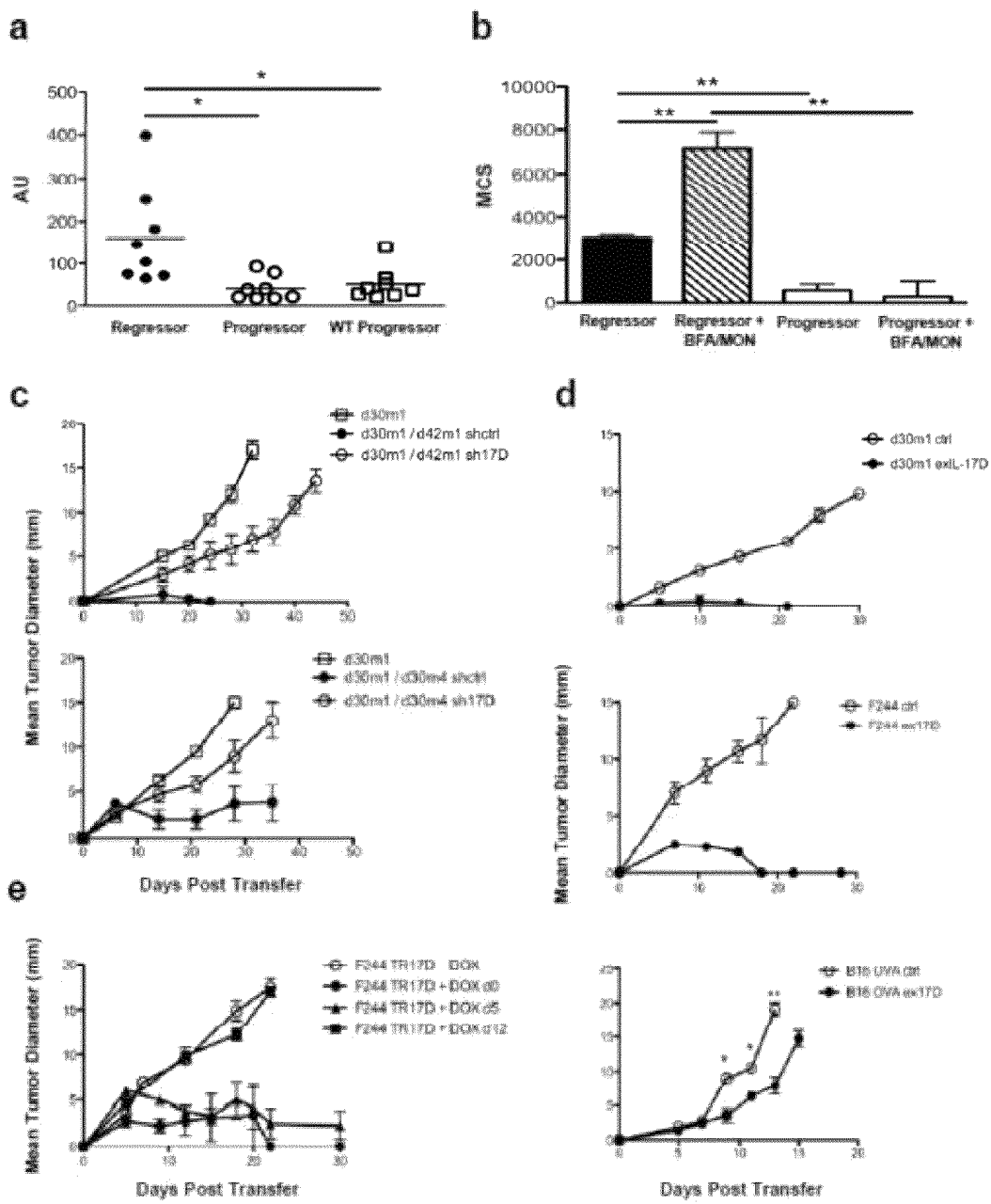
Fig. 1a-e a b

USE OF IL-17D FOR THE TREATMENT AND PREVENTION OF CANCERS

CROSS-REFERENCE TO RELATED APPLICATIONS

This application is a U.S. National Phase under 35 U.S.C. §371 of Intl. Appl. No. PCT/US2012/031407, filed on Mar. 30, 2012, which claims the benefit of U.S. Provisional Application No. 61/469,531, filed on Mar. 30, 2011, which are hereby incorporated herein by reference in their entirety for all purposes.

SEQUENCE LISTING

The instant application contains a Sequence Listing which has been submitted in ASCII format via EFS-Web and is hereby incorporated by reference in its entirety. Said ASCII copy, created on Sep. 30, 2013, is named UCSCP019_SL.txt and is 4,666 bytes in size.

FIELD OF THE INVENTION

The present invention relates to the treatment and prevention of cancers, particularly cancers whose growth is reduced or inhibited by immunostimulatory therapy, by the administration of interleukin-17D (IL-17D), compounds that can increase the production, half-life, or activity of IL-17D, or compositions that contain IL-17D.

BACKGROUND OF THE INVENTION

Of the interleukin-17 cytokine family, the functions of IL-17B, IL-17C, and IL-17D remain largely elusive. Iwakura, et al., *Immunity* (2011) 34(2):149-62. Little is known about the role of IL-17 in de novo carcinogenesis. The role of T helper type 17 cells, which produce interleukin-17A (IL-17A) in particular, has been controversial. Wang and colleagues have found that IL-17A supports cancer-associated inflammation in the tumor microenvironment, enhancing tumor development in carcinogen-induced skin cancer. Wang, *Cancer Res.* (2010) 70(24):10112-20. In another study, Zhu, et al., concludes that IL-17A expression by breast-cancer-associated macrophages promotes invasiveness of breast cancer cell lines. Zhu, et al., *Breast Cancer Research* (2008) 10(6):R95. There are no published studies on the role of IL-17D in cancer prevention or therapy.

The process of cancer immunoediting generates a repertoire of cancer cells that can persist in immune competent hosts (Shankaran, V. et al. *Nature* (2001) 410:1107-1111; Dunn, et al., *Nature Immunol.* (2002) 3:991-998; Koebel, et al., *Nature* (2007) 450, 903-907; Vesely, et al., *Annu. Rev. Immunol.* (2011) 29:235-271; Schreiber, et al., *Science* (2011) 331:1565-1570). In its most complex form, cancer immunoediting involves the initial elimination of immunogenic tumor cells, followed by a state of equilibrium, whereby tumor cells and immune cells co-exist without apparent growth of the tumor mass, and ending in escape, whereby immune evasive cancers arise. When cancer immunoediting is impaired in immune deficient hosts, the resultant tumor cell repertoire is "unedited" and contains highly immunogenic cancer cells. For example, 3'methylcholanthrene (MCA)-induced sarcomas that develop in WT mice are edited and poorly immunogenic whereas similar sarcomas that develop in immune deficient RAG2-/- mice are unedited and highly immunogenic (Shankaran et al., *Nature* 2001, supra). In these studies, the immunogenicity of the tumor cell lines was determined by transplanting them into WT mice, leading to the definition of "progressor" tumor cell lines as edited cells that evade the immune system and "regressor" cell lines as unedited cell lines that cannot grow when transplanted in WT mice but can grow in immune deficient mice. Thus, progressor cells represent the typical cancer cell that arises in human cancer patients with an intact immune system, whereas regressor cells (often derived from immune deficient mice) are unique cells that can activate the immune system to induce tumor rejection. Indeed, immune cells can efficiently infiltrate, recognize, become activated, and eliminate regressor but not progressor tumor cells (Bui, et al., *Cancer Res* (2006) 66:7301-7309; Koebel, et al., *Nature* (2007) 450:903-907; Vesely, et al., *Annu. Rev. Immunol.* (2011) 29:235-271; Schreiber, et al., *Science* (2011) supra) but it is not known how tumor-expressed genes can influence each of these steps. In particular, the molecular differences between edited and unedited tumor cells are poorly defined.

SUMMARY OF THE INVENTION

In one aspect, the invention provides methods of preventing, delaying, inhibiting and/or reducing the growth and/or proliferation of a cancer in a subject comprising administering to the subject an effective amount of interleukin-17D ("IL-17D").

In a further aspect, the invention provides methods of preventing, delaying, inhibiting or reducing the growth and/or proliferation of a cancer cell comprising contacting the cancer cell with an effective amount of IL-17D.

In another aspect, the invention provides methods of preventing, delaying, inhibiting and/or reducing the growth and/or proliferation of a cancer in a subject and/or methods of preventing, delaying, inhibiting or reducing the growth and/or proliferation of a cancer cell comprising administering to the subject and/or contacting the cancer cells with a compound that stimulates or augments the production or activity of IL-17D. Illustrative compounds include, e.g., an antibody or binding protein that binds to and stabilizes IL-17D, or encapsulated Polyinosinic:polycytidylic acid ("poly (I:C)") that stimulates or augments production of IL-17D. In various embodiments, the poly (I:C) is encapsulated in a liposome or a nanoparticle.

In various embodiments, the IL-17D mediates tumor rejection and the prevention, delay, inhibition and/or reduction of the growth or proliferation of a cancer or cancer cell through recruitment of natural killer (NK) cells. For example, IL-17D promotes the recruitment of NK cells to the site of the tumor, metastasis or cancer cell, thereby promoting the rejection and/or inhibiting, reducing, preventing and/or delaying the growth or proliferation of the tumor, metastasis or cancer cell.

With respect to the embodiments, in some embodiments, the subject has the cancer. In some embodiments, the subject has a predisposition for developing the cancer, for example, the subject is in remission from the cancer. In some embodiments, the subject is suspected of having the cancer, or at risk of developing the cancer. Administering an effective amount of IL-17D can prevent and/or delay a relapse of the cancer.

The methods are useful to reduce, inhibit and/or prevent the growth of cancers responsive to immunostimulatory therapies. For example, in some embodiments, the cancer expresses a tumor-associated antigen. In some embodiments, the cancer is an epithelial cancer. In some embodiments, the cancer is a melanoma. In some embodiments, the cancer is a sarcoma. In some embodiments, the cancer is a hematologic malignancy. In some embodiments, the cancer is a glioma.

The IL-17D can be administered to the subject via any method known in the art. For example, in some embodiments, a polynucleotide encoding IL-17D can be transduced into a cell, and the cell expressing IL-17D can be transplanted into the subject, for example, in the vicinity of the tumor to be regressed or killed. The transduced cell can be a cancerous or non-cancerous cell. In some embodiments, the transduced cell is a tumor cell. Preferably, the transduced tumor cell is a regressor tumor cell. In some embodiments, the IL-17D is administered to the subject as a polypolypeptide. As appropriate or desired, the IL-17D polypeptide can be administered intravenously, intratumorally, intramuscularly, subcutaneously, intradermally, or inhalationally. In some embodiments, a polynucleotide encoding IL-17D is administered to the subject. As appropriate or desired, the polynucleotide encoding IL-17D can be administered intravenously, intratumorally, intramuscularly, subcutaneously, intradermally, or inhalationally. In some embodiments, the polynucleotide encoding IL 17D is in a virus. In some embodiments, the polynucleotide encoding IL 17D is in a plasmid.

In some embodiments, the methods do not comprise administering one or more of IL-17A, IL-17B, IL-17C, IL-17E, or IL-17F. In some embodiments, the methods do not comprise administering a cytokine other than IL-17D. In some embodiments, the IL-17D is not a component of a conjugate, e.g., to an antibody or antibody fragment or to a toxic moiety. In some embodiments, the IL-17D is administered or contacted as a component of a conjugate or fusion protein, e.g., to an antibody or antibody fragment, a toxic moiety, or an antineoplastic agent. In some embodiments, the IL-17D is conjugated or fused to an antibody or antibody fragment that binds to a tumor specific antigen.

In some embodiments, compounds that stimulate or augment the production or activity of IL-17D are administered. For example, an antibody that binds to IL-17D can stabilize the cytokine and augment function. In various embodiments, agonists of virus infection, e.g., ligands for the RIG-like cytoplasmic receptors, can induce IL-17D. In some embodiments, the ligand for the RIG-like cytoplasmic receptor is encapsulated poly (I:C). In various embodiments, the poly (I:C) is encapsulated in a liposome or a nanoparticle.

Definitions

The term "interleukin-17D" refers to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 300, 400, or more amino acids, or over the full-length, to an amino acid sequence encoded by a IL-17D nucleic acid (see, e.g., GenBank Accession No. NM_138284.1) or to an amino acid sequence of a IL-17D polypeptide (see e.g. GenBank Accession No. NP_612141.1); (2) bind to antibodies, e.g., polyclonal antibodies, raised against an immunogen comprising an amino acid sequence of a IL-17D polypeptide (e.g., IL-17D polypeptides described herein); or an amino acid sequence encoded by a IL-17D nucleic acid (e.g., IL-17D polynucleotides described herein), and conservatively modified variants thereof; (3) specifically hybridize under stringent hybridization conditions to an anti-sense strand corresponding to a nucleic acid sequence encoding a IL-17D protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a IL-17D nucleic acid (e.g., IL-17D polynucleotides, as described herein, and IL-17D polynucleotides that encode IL-17D polypeptides, as described herein).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W); and
7) Serine (S), Threonine (T)

(see, e.g., Creighton, Proteins (1984)).

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., an IL-17D polynucleotide or polypeptide sequence as described herein, when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, for example, over a region that is 50-100 amino acids or nucleotides in length, or over the full-length of a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to IL-17D nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., eds., Current Protocols in Molecular Biology (1995 supplement)).

Examples of algorithms that are suitable for determining percent sequence identity and sequence similarity are the BLAST and BLAST 2.0 algorithms, which are described in Altschul et al., J. Mol. Biol. 215:403-410 (1990) and Altschul et al., Nucleic Acids Res. 25:3389-3402 (1977), respectively. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=-2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "cancer" or "cancer cell" is used herein to denote a tissue or cell found in a neoplasm which possesses characteristics which differentiate it from normal tissue or tissue cells. Among such characteristics include but are not limited to: degree of anaplasia, irregularity in shape, indistinctness of cell outline, nuclear size, changes in structure of nucleus or cytoplasm, other phenotypic changes, presence of cellular proteins indicative of a cancerous or pre-cancerous state, increased number of mitoses, and ability to metastasize. Words pertaining to "cancer" include carcinoma, sarcoma, tumor, epithelioma, leukemia, lymphoma, polyp, and scirrus, transformation, neoplasm, and the like.

The terms "cancer-associated antigen" or "tumor-associated antigen" or "tumor-specific marker" or "tumor marker" interchangeably refers to a molecule (typically protein, carbohydrate or lipid) that is preferentially expressed on the surface of a cancer cell in comparison to a normal cell, and which is useful for the preferential targeting of a pharmacological agent to the cancer cell. Oftentimes, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. Oftentimes, a cancer-associated antigen is a cell surface molecule that is inappropriately synthesized in the cancer cell, for instance, a molecule that contains deletions, additions or mutations in comparison to the molecule expressed on a normal cell. Oftentimes, a cancer-associated antigen will be expressed exclusively on the cell surface of a cancer cell and not synthesized or expressed on the surface of a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal.

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and broadly encompasses naturally-occurring forms of antibodies (for example, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprise any modified or derivatised variants thereof that retains the ability to specifically bind an epitope. Antibody derivatives may comprise a protein or chemical moiety conjugated to an antibody. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, F(ab')$_2$ fragments, disulfide-linked Fvs (sdFv) fragments, for example, as produced by a Fab expression library, anti-idiotypic (anti-Id) antibodies, intrabodies, nanobodies, synthetic antibodies, and epitope-binding fragments of any of the above.

A "regressor" tumor cell refers to a tumor cell that is rejected when transplanted into an individual. In certain instances, this may be due to the antigenicity of the regressor tumor cell. See, e.g., Chen, *Cancer Res*. (1990) 50(5):1544-9; Mullen, et al., *Cell Immunol*. (1989) 119(1):101-13; Kaba, et al, *Cancer Res*. (1990) 50(11):3159-66; and Shankaran, et al., *Nature* (2001) 410(6832):1107-11.

The term "individual," "patient,", "subject" interchangeably refer to a mammal, for example, a human, a non-human primate, a domesticated mammal (e.g., a canine or a feline), an agricultural mammal (e.g., equine, bovine, ovine, porcine), or a laboratory mammal (e.g., *rattus*, murine, lagomorpha, hamster).

The term "isolated," and variants thereof denotes that the IL-17D polypeptide or polynucleotide is essentially free of other cellular components with which it is associated in the natural state. It is preferably in a homogeneous state. It can be in either a dry or aqueous solution. Purity and homogeneity are typically determined using known techniques, such as polyacrylamide gel electrophoresis or high performance liquid chromatography. A protein or polynucleotide that is the predominant species present in a preparation is substantially purified.

The term "purified" denotes that a polypeptide or polynucleotide gives rise to essentially one band in an electrophoretic gel. Particularly, it means that the nucleic acid or protein is at least 80%, 85% or 90% pure, more preferably at least 95% pure, and most preferably at least 99% pure.

The terms "systemic administration" and "systemically administered" refer to a method of administering IL-17D to a mammal so that the polypeptide or polypeptide composition is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administer" and "co-administering" and variants thereof refer to the simultaneous presence of two or more active agents in the blood of an individual. The active agents that are co-administered can be concurrently or sequentially delivered. As used herein, IL-17D can be co-administered with another active agent efficacious in treating or preventing cancer (e.g., an antibody against a tumor associated antigen, one or more cytokines other than IL-17D, or a chemotherapeutic agent).

The term "effective amount" or "pharmaceutically effective amount" refer to the amount and/or dosage, and/or dosage regime of one or more compounds necessary to bring about the desired result e.g., an amount sufficient to mitigating in a mammal one or more symptoms associated with cancer, or an amount sufficient to lessen the severity or delay the progression of cancer in a mammal (e.g., therapeutically effective amounts), an amount sufficient to reduce the risk or delaying the onset, and/or reduce the ultimate severity of cancer in a mammal (e.g., prophylactically effective amounts).

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The terms "treating" and "treatment" and variants thereof refer to delaying the onset of, retarding or reversing the progress of, alleviating or preventing either the disease or condition to which the term applies, or one or more symptoms of such disease or condition. Treating and treatment encompass both therapeutic and prophylactic treatment regimens.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced in comparison to the tumor burden prior to administration of IL-17D. In some embodiments, the growth, progression or spread of a tumor or cancer is inhibited, reduced or decreased by at least about 1-fold, 2-fold, 3-fold, 4-fold, or more in comparison to the tumor burden prior to administration of the IL-17D.

BRIEF DESCRIPTION OF THE DRAWINGS

FIGS. 1A-F illustrate that IL-17D is expressed in rejecting tumors, is required for rejection of tumor mixtures, and is sufficient to induce rejection when overexpressed in MCA sarcoma cell lines. (a) Microarray data showing higher levels of IL-17D in regressor versus progressor tumor cell lines cultured in vitro. (b) Intracellular flow cytometry showing higher levels of IL-17D protein in regressor versus progressor tumor cells with and without secretory pathway blockers. (c) Mixtures of regressor and progressor are rejected via an IL-17D-dependent mechanism. The progressor d30m1 was transplanted into syngeneic WT mice by itself or with a regressor (d42m1-top graph, d30m4-bottom graph) that was transduced with control (shctrl) shRNA or shRNA specific for IL-17D, and tumor growth was measured. (d) Overexpression of IL-17D led to tumor rejection or growth delay. The indicated progressor tumor cell lines were transduced with control of IL-17D-overexpressing constructs and transplanted into syngeneic WT mice. (e) Rejection mediated by IL-17D occurs with small but not large tumors. The progressor F244 containing a dox-regulatable IL-17D gene was transplanted into mice, and dox was given at day 0, 5, and 12 to induce IL-17D. (f) Rejection of progressor-regressor mixtures is spatially localized. Tumor growth of d30m1 progressor unmixed or mixed with d42m1 and injected into WT mice on the right and left flank respectively in the same mouse.

DETAILED DESCRIPTION

1. Introduction

Figure 1F:
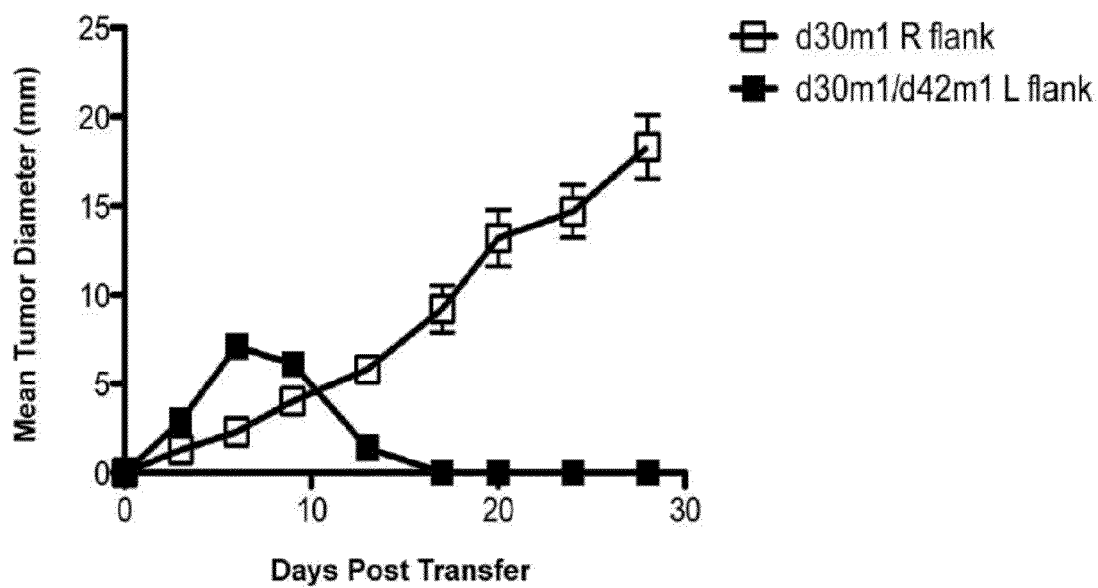

The present invention is based, in part, on the discovery that the cytokine IL-17D is active in reducing, inhibiting, preventing and/or delaying the growth or proliferation of cancer cells and/or tumors.

Immune system interaction with cancers can either enhance or prevent tumor formation. Cytokine secretion by immune infiltrates and tumor cells are important in regulating this process. IL-17A, a pro-inflammatory member of the IL-17 family, has been shown to have conflicting results in regards to cancer progression or regression. Prior to the present invention, other members of the IL-17 family, in particular IL-17D, were not known to have a role in immune responses to cancer, or endogenous function. The present discovery of the antitumor effects of IL-17D is based, in part, on the use of histologically matched methylcholanthrene (MCA)-induced tumor cell lines that will continuously grow (Progressors) or reject (Regressors) after transplantation into syngeneic WT mice. These regressor cell lines can grow in immune deficient RAG2−/− mice, indicating that their rejection in WT mice requires an intact immune system. We have used these cell lines to identify differential cytokine expression profiles from microarray analysis. Data provided herein shows IL-17D transcript and protein are significantly overexpressed in regressor cell lines when compared to progressor cell lines. Overexpression of IL-17D in progressor tumor cell lines leads to their rejection in WT mice in a NK cell dependent manner. The present invention is based, in part, on the recognition that IL-17D expression in regressor cell lines leads to immune-mediated tumor rejection by recruiting NK cells that polarize M1 macrophages in the tumor microenvironment.

2. Subjects Amenable to Treatment or Prevention

In various embodiments, subjects who can benefit from treatment by administration of IL-17D already have cancer, and/or have received a positive diagnosis of cancer. Subject presenting with cancer may or may not exhibit symptoms. In some embodiments, subjects who can benefit from a preventative regime of administration of IL-17D are at risk of developing cancer, e.g., due to familial history, genetic predisposition, or past personal history of having cancer.

Patients who can benefit from a treatment regime may already present with symptoms of cancer. For example, evidence of cancer or a tumor may be present (by visual inspection or palpation, or by scanning techniques, e.g., magnetic resonance imaging (MRI) or Positron Emission Tomography (PET) scans). In various embodiments, the subject has received a positive diagnosis of cancer.

In other cases, the patient who may benefit from a preventative regime may have a personal or familial history of cancer. For example, the patient may be in remission following successful therapeutic treatment of the cancer. In various embodiments, the patient may have tested positive for a gene associated with increased risk of cancer or the recurrence of cancer.

3. Conditions Subject to Prevention or Treatment

IL-17D finds use in the treatment of cancer. IL-17D can be administered to a patient to effect the inhibition, reduction, retraction or prevention of proliferation or growth of a tumor or a cancer cell. Administration of IL-17D finds use in treating or preventing cancers that are inhibited by immunostimulatory therapies. Illustrative cancers include those that express tumor associated antigens. Exemplary cancers include carcinomas, sarcomas, adenocarcinomas, hematologic malignancies, lymphomas, leukemias, etc., including solid and lymphoid cancers, skin, kidney, breast, lung, kidney, bladder, colon, ovarian, prostate, pancreas, stomach, brain, glioma, head and neck, skin, uterine, testicular, esophagus, and liver cancer, lymphoma, including non-Hodgkins and Hodgkins lymphoma, leukemia, and multiple myeloma. Of interest are epithelial cancers (e.g., carcinomas), for example, of skin (e.g., squamous cell carcinoma), thyroid, adrenal, bladder, uterus, breast, prostate and liver tissues and non-epithelial cancers such as melanoma, sarcoma, and glioma.

Modern methods for cancer immunotherapy are based on the principle that the immune system can detect and defend against spontaneous tumors. Evidence supporting the concept of "Immunological surveillance" (see, Burnet F M Lancet 1:1171-4, 1967), comes in part from epidemiological studies indicating that the incidence of cancer increases in patients that are immunocompromised by disease, such as infection (see, Klein G. Harvey Lect. 69:71-102, 1975; and Kuper et al., J. Intern. Med. 248:171-83, 2000), or following medical interventions such as bone marrow ablation (see, Birkeland et al., Lancet 355:1886-7, 2000; and Penn I, Cancer Detect Prev. 18:241-52, 1994). Experiments performed in gene-targeted mice also show that the immune system modulates susceptibility to spontaneous tumors in aged mice (see, Smyth, M. et al., J. Exp. Med. 192:755-760, 2000; and Davidson, W. et al., J. Exp. Med. 187: 1825-1838, 1998) or following exposure to chemical carcinogens (see, Peng, S et al., J. Exp. Med. 184: 1149-1154, 1996; Kaplan, D. et al., Proc. Nat. Acad. Sci. USA 95:7556-7561, 1998; and Shankaran V. et al., Nature 410:1107-1111, 2001). Proof that immune recognition of tumors occurs frequently in tumor bearing hosts comes from the identification of T-cells that are reactive to a broad range of tumor associated antigens including differentiation antigens, mutational antigens, tissue-specific antigens, cancer-testis antigens, self-antigens that are over-expressed in tumors, and viral antigens (Boon T. et al., Immunol Today 18:267-8, 1997). In addition, B-cells are known to produce high titers of circulating IgG antibodies that recognize these same classes of tumor antigens (Stockert E. et al., J. Exp. Med. 187:1349-54, 1998; Sahin U et al., Curr. Opin. Immunol 9:709-16, 1997; and Jager, E. et al., Proc. Nat. Acad. Sci. USA 97:12198-12203, 2000), and NK cells have been isolated that can recognize and kill tumor cells that express various stress-related genes (Bauer, S et al., Science 285:727-729, 1999).

The concept that immunotherapy can be an effective method for treating cancer is firmly established in experimental animal models, and while the methodologies are much less advanced for human subjects, there is a strong suggestion that the immune system can be stimulated to reject established disease. The very first attempt at cancer immunotherapy was reported by William Coley in 1893 who, using extracts of pyogenic bacteria, achieved anti-cancer responses most likely through the induction of systemic inflammation and cell-mediated immunity (Coley W B. The treatment of malignant tumors by repeated inoculations of erysipelas. With a report of ten original cases. 1893, Clin Orthop. 262:3-11, 1991). In more modern times five generalized strategies have been employed to increase the numbers of effector cells and/or modulate their anti-cancer activity (reviewed in Rosenberg, S A. (Ed.), Principles and practice of the biologic therapy of cancer, 3rd edition, Lippincott Williams & Wilkins, Philadelphia, Pa., 2000): cytokine therapy, cell transfer therapy, monoclonal antibody therapy, cancer vaccines, and gene therapy. To date, each method has shown effectiveness in mediating an anti-cancer response although the durability of these responses, with a few exceptions, is mostly temporary. This fact reflects our limited understanding of tumor immunology and argues that improvements in the technology await the utilization of previously unrecognized elements of the anti-cancer response. The present invention provides such an element to improve our understanding of tumor immunology as well as provide IL-17D polypeptides and polynucleotides that are therapeutically useful in treating and preventing human cancers.

In the context of effecting treatment, the patient has a cancer or a tumor burden, and administration of the polypeptide fraction or one or more of the polypeptides can reverse, delay or inhibit progression of the disease. In the context of effecting prevention, the patient may be in remission, or may have undergone the removal of a primary tumor, and administration of the polypeptide fraction or the one or more polypeptides can reduce, inhibit or eliminate growth of metastasis.

Exemplary cancers that can be treated or prevented by contacting with IL-17D include without limitation lymphoma, lung cancer, breast cancer, ovarian cancer, gastric and intestinal cancers (including colon cancer and rectal cancer), hepatic cancer, esophageal cancer, bladder cancer, renal cancer, head and neck cancers. In some embodiments, the cancer produces solid tumors. In some embodiments, the cancer is an epithelial cancer or a carcinoma, a sarcoma, a glioma or a hematological cancer.

Exemplary hematologic malignancies that can be treated or prevented by contacting with IL-17D include without limitation lymphomas (such as but not limited to, non-Hodgkin's lymphoma, including Burkitt's lymphoma, and Hodgkin's lymphoma, as well as all subtypes associated with each), acute lymphocytic leukemia (ALL), chronic lymphocytic leukemia (CLL), acute myeloid leukemia (AML), chronic myeloid leukemia (CML), and adult T-cell leukemia lymphoma.

Exemplary lung cancers that can be treated or prevented by contacting with IL-17D include without limitation adenocarcinoma, squamous carcinoma, bronchial carcinoma, bronchoalveloar carcinoma, large cell carcinoma, small-cell carcinoma, nonsmall cell lung carcinoma and metastatic lung cancer refractory to conventional chemotherapy.

Exemplary hematological cancers that can be treated or prevented by contacting with IL-17D include without limitation leukemia, multiple myeloma and plasmocytoma.

Exemplary sarcomas that can be treated or prevented by contacting with IL-17D include without limitation rhabdomyosarcoma, osteosarcoma, chondrosarcoma, myosarcoma, liposarcoma, fibrosarcoma and Ewing's sarcoma.

Exemplary gastric, digestive and intestinal cancers that can be treated or prevented by contacting with IL-17D include without limitation intestinal carcinoma, rectal carcinoma, colon carcinoma, familial adenomatous polyposis carcinoma, hereditary non-polyposis colorectal cancer, gastric carcinoma, craniopharyngioma, gall bladder carcinoma, esophageal carcinoma, pancreatic carcinoma and adenocarcinoma (including adenocarcinomas of the esophagus and stomach).

Exemplary cancers of the head and neck that can be treated or prevented by contacting with IL-17D include without limitation larynx carcinoma, hypopharynx carcinoma, tongue carcinoma and salivary gland carcinoma.

Exemplary urogenital cancers that can be treated or prevented by contacting with IL-17D include without limitation labial carcinoma, ovarian carcinoma, cervix carcinoma, uterine corpus carcinoma, endometrium carcinoma, chorion carcinoma, prostate carcinoma, testis carcinoma, seminoma, urinary carcinoma, kidney carcinoma, renal carcinoma, and adenocarcinoma (including adenocarcinomas of the vagina, cervix, prostate, and urachus).

Exemplary nervous and sensory system cancers that can be treated or prevented by contacting with IL-17D include without limitation neuroblastoma, brain tumors, meningioma, ependymoma, medulloblastoma, peripheral neuroectodermal tumors, glioblastoma, astrocytoma, glioma, oligodendroglioma and retinoblastoma.

Exemplary endocrine and glandular tissue cancers that can be treated or prevented by contacting with IL-17D include without limitation pancreatic carcinoma, medullary thyroid carcinoma, follicular thyroid carcinoma, anaplastic thyroid carcinoma, papillary thyroid carcinoma, pheochromocytoma, adrenal tumors and adenocarcinoma.

Exemplary hepatic cancers that can be treated or prevented by contacting with IL-17D include without limitation hepatocellular carcinoma.

Exemplary skin cancers that can be treated or prevented by contacting with IL-17D include without limitation melanoma, basal cell carcinoma, squamous cell carcinoma and choroids melanoma.

Additional cancers that can be treated or prevented by contacting with IL-17D include without limitation teratomas.

4. Administration of IL-17D a. Uses of IL-17D in the Treatment and Prevention of Cancers Examples of methods for using IL-17D in the treatment and prevention of cancer include, but are not limited to, the following:

IL-17D can be used as a single agent for direct inhibitory activity against tumors that express the IL-17D receptor. Administration in a pharmaceutical vehicle for therapeutic use can be achieved using methods in the art and described herein.

IL-17D can be conjugated to a toxic compound that binds and kills tumor cells, e.g., tumors that express IL-17D receptor. The toxic compound can be an antineoplastic agent; a radioisotope (e.g., $^{125}$I, $^{90}$Y) or a protein toxin such as (e.g., Ricin A, Pseudomonas exotoxin, or diphtheria B toxin). The attachment of these toxic compounds to IL-17D might occur through chemical conjugation (Rapley R. Mol. Biotechnol. 3:139-54, 1995) or genetic recombination (Foss F M. Clin. Lymphoma Suppl 1:S27-31, 2000). Such toxin conjugates with IL-17D can be used to kill various tumors in vivo and in vitro (see, e.g., U.S. Pat. No. 6,307,024).

IL-17D can be used as an immunostimulatory agent for cancer monotherapy. A variety of cytokines such as IL-1, IL-2, IL-4, IL-6, IL-8, IL-12, IL-15, IL-21, TNF (e.g., TNF-α, TNF-β and interferon (including, e.g., both Type I and Type II interferon; IFN-α, IFN-β, IFN-γ), are known to stimulate anti-cancer responses in animal models via stimulation of the immune system (reviewed in Rosenberg, S A ibid.). IL-17D also stimulates the immune system. In various embodiments, IL-17D is co-administered with one or more cytokines selected from IL-1, IL-2, IL-4, IL-6, IL-8, IL-12, IL-15, IL-21, TNF (e.g., TNF-α, TNF-β) and interferon (including, e.g., both Type I and Type II interferon; IFN-α, IFN-β, IFN-γ). Cytokine monotherapy is an accepted practice for human cancer patients. For example, the use of IL-2 and IFN-α are used for the treatments of metastatic melanoma and renal cell carcinoma (e.g., see, Atkins M B et al., J. Clin. Oncol. 17:2105-16, 1999; Fyfe G et al., J. Clin. Oncol. 13:688-96, 1995; and Jonasch E, and Haluska F G, Oncologist 6:34-55, 2001). The mechanism of action of these cytokines includes, but is not limited to, an enhancement of Th1 cell-mediated responses including direct tumor cell killing by CD8+T-cells and NK cells. IL-17D can be used therapeutically or clinically to actively kill tumor cells in human disease, and to regulate these activities, as well as in additional anti-cancer responses.

IL-17D can be used as an immunostimulatory agent in combination with surgery, chemotherapy, radiation, and myeloablation. In addition to working alone to boost anti-cancer immunity in patients, IL-17D can work in synergy with standard types of chemotherapy or radiation. For instance, in preclinical models of lymphoma and renal cell carcinoma, the combination of IL-2 with doxorubicin (Ehrke M J et al., Cancer Immunol. Immunother. 42:221-30, 1996), or the combinations of IL-2 (Younes E et al., Cell Immunol. 165:243-51, 1995) or IFN-α (Nishisaka N et al., Cytokines Cell Mol. Ther. 6:199-206, 2000) with radiation provided superior results over the use of single agents. In this setting, IL-17D can further reduce tumor burden and allow more efficient killing by the chemotherapeutic. Additionally, lethal doses of chemotherapy or radiation followed by bone marrow transplantation or stem cell reconstitution could reduce tumor burden to a sufficiently small level (i.e., minimal residual disease) to better allow an IL-17D mediated anti-cancer effect. Examples of this type of treatment regimen include the uses of IL-2 and IFN-α to modify anti-cancer responses following myeloablation and transplantation (Porrata L F et al., Bone Marrow Transplant. 28:673-80, 2001; Slavin S, and Nagler A. Cancer J. Sci. Am. Suppl 1:S59-67, 1997; and Fefer A et al., Cancer J. Sci. Am. Suppl 1:S48-53, 1997). In the case of lymphoma and other cancers, depending on when IL-17D is used relative to the chemotherapeutic agents, IL-17D may be employed to directly synergize with the chemotherapeutic agent's effect on the tumor cells or alternatively employed after the chemotherapy to stimulate the immune system. Those skilled in the art would design a protocol to take advantage of both possibilities.

IL-17D can be used in combination with other immunomodulatory compounds including various cytokines and co-stimulatory/inhibitory molecules. The immunostimulatory activity of IL-17D in mediating an anti-cancer response can be enhanced in patients when IL-17D is used with other classes of immunomodulatory molecules. These could include, but are not limited to, the use of additional cytokines. For instance, the combined use of IL-2 and IL-12 shows beneficial effects in T-cell lymphoma, squamous cell carcinoma, and lung cancer (Zaki M H et al., J. Invest. Dermatol. 118:366-71, 2002; Li D et al., Arch. Otolaryngol. Head Neck Surg. 127:1319-24, 2001; and Hiraki A et al., Lung Cancer 35:329-33, 2002). In addition IL-17D could be combined with reagents that co-stimulate various cell surface molecules found on immune-based effector cells, such as the activation of CD137 (Wilcox R A et al., J. Clin. Invest. 109:651-9, 2002) or inhibition of CTLA4 (Chambers C A et al., Ann. Rev. Immunol. 19:565-94, 2001). Alternatively, IL-17D could be used with reagents that induce tumor cell apoptosis by interacting with TRAIL-related receptors (Takeda K et al., J. Exp. Med. 195:161-9, 2002; and Srivastava R K, Neoplasia 3:535-46, 2001). Such reagents include TRAIL ligand, TRAIL ligand-Ig fusions, anti-TRAIL antibodies, and the like.

IL-17D can be used in combination with Monoclonal Antibody Therapy. Treatment of cancer with monoclonal antibodies is becoming a standard practice for many tumors including Non-Hodgkins lymphoma (RITUXAN™, rituximab), forms of leukemia (MYLOTARG™, gemtuzumab ozogamicin), breast cell carcinoma (HERCEPTIN™, trastuzumab), and colon carcinoma (ERBITUX™, cetuximab). One mechanism by which antibodies mediate an anti-cancer effect is through a process referred to as antibody-dependent cell-mediated cytotoxicity (ADCC) in which immune-based cells including NK cells, macrophages and neutrophils kill those cells that are bound by the antibody complex. Due to its immunomodulatory activity, IL-17D can be used to enhance the effectiveness of antibody therapy. Examples of this type of treatment paradigm include the combination use of RITUXAN™ and either IL-2, IL-12, or IFN-α for the treatment of Hodgkin's and Non-Hodgkin's lymphoma (Keilholz U et al., Leuk. Lymphoma 35:641-2, 1999; Ansell S M et al., Blood 99:67-74, 2002; Carson W E et al., Eur. J. Immunol. 31:3016-25, 2001; and Sacchi S et al., Haematologica 86:951-8., 2001). IL-17D can be used therapeutically or clinically to enhance the activity and effectiveness of antibody therapy in human disease. In various embodiments, IL-17D can be conjugated or fused to an antibody, antibody fragment or protein that is specific for a tumor, thereby delivering it to the tumor.

Generally, therapeutic antibodies or antibody fragments that specifically bind to a tumor-associated antigen ("TAA") find use as conjugates or fusion proteins with IL-17D. Examples of known TAAs include without limitation, melanoma associated antigens (MAGE-1, MAGE-3, TRP-2, melanosomal membrane glycoprotein gp100, gp75 and MUC-1 (mucin-1) associated with melanoma); CEA (carcinoembryonic antigen) which can be associated, e.g., with ovarian, melanoma or colon cancers; folate receptor alpha expressed by ovarian carcinoma; free human chorionic gonadotropin beta (hCGβ) subunit expressed by many different tumors, including but not limited to myeloma; HER-2/neu associated with breast cancer; encephalomyelitis antigen HuD associated with small-cell lung cancer; tyrosine hydroxylase associated with neuroblastoma; prostate-specific antigen (PSA) associated with prostate cancer; CA125 associated with ovarian cancer; and the idiotypic determinants of a B cell lymphoma can generate tumor-specific immunity (attributed to idiotype-specific humoral immune response). Moreover, antigens of human T cell leukemia virus type 1 have been shown to induce specific CTL responses and antitumor immunity against the virus-induced human adult T cell leukemia (ATL). See, e.g., Haupt, et al., *Experimental Biology and Medicine* (2002) 227:227-237; Ohashi, et al., *Journal of Virology* (2000) 74(20):9610-9616.

Illustrative antibodies that can be conjugated or fused to IL-17D include without limitaton HERCEPTIN™ (Trastuzumab) (Genentech, Calif.) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ (edrecolomab) which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ (LM609 anti-$\alpha_v\beta_3$ which is a humanized anti-$\alpha V\beta 3$ integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ (rituximab) which is a chimeric anti-CD20 IgG1 antibody (IDEC Pharm/Genentech, Roche/Zettyaku); LYMPHOCIDE™ (epratuzumab) which is a humanized anti-CD22 IgG antibody (Immunomedics); ICM3 is a humanized anti-ICAM3 antibody (ICOS Pharm); IDEC-114 is a primatized anti-CD80 antibody (IDEC Pharm/Mitsubishi); ZEVALIN™ (ibritumomab tiuxetan) is a radiolabelled murine anti-CD20 antibody (IDEC/Schering AG); IDEC 131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-$\alpha$ antibody (CAT/BASF); CDP870 is a humanized anti-TNF-$\alpha$ Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-$\alpha$ IgG4 antibody (Celltech); LDP-02 is a humanized anti-$\alpha 4\beta 7$ antibody (LeukoSite/Genentech); OrthoClone OKT4A is a humanized anti-CD4 IgG antibody (Ortho Biotech); ANTOVA™ (ruplizumab) is a humanized anti-CD40L IgG antibody (Biogen); ANTEGREN™ (natalizumab) is a humanized anti-VLA-4 IgG antibody (Elan); and CAT-152 is a human anti-TGF-$\beta 2$ antibody (Cambridge Ab Tech).

IL-17D can be used in combination with cell adoptive therapy. One method used to treat cancer is to isolate anticancer effector cells directly from patients, expand these in culture to very high numbers, and then to reintroduce these cells back into patients. The growth of these effector cells, which include NK cells, LAK cells, and tumor-specific T-cells, requires cytokines such as IL-2 (Dudley M E et al., J. Immunother. 24:363-73, 2001). Given its chemotactic and potential growth stimulatory properties on certain lymphocytes such as NK cells, IL-17D could also be used to propagate these cells in culture for subsequent re-introduction into patients in need of such cells. Following the transfer of cells back into patients, methods are employed to maintain their viability by treating patients with cytokines such as IL-2 (Bear H D et al., Cancer Immunol Immunother. 50:269-74, 2001; and Schultze J L et al., Br. J. Haematol. 113:455-60, 2001). Again, IL-17D can be used following or concomitant with adoptive therapy to increase effector cell function and survival.

IL-17D can be used in combination with tumor vaccines. The major objective of cancer vaccination is to elicit an active immune response against antigens expressed by the tumor. Numerous methods for immunizing patients with cancer antigens have been employed, and a variety of techniques are being used to amplify the strength of the immune response following antigen delivery (reviewed in Rosenberg, S A ibid). Methods in which IL-17D can be used in combination with a tumor vaccine include, but are not limited to, the delivery of autologous and allogeneic cells (e.g., non-cancerous or tumor cells) that either express the IL-17D gene or in which IL-17D is delivered in the context of an adjuvant protein. Similarly, IL-17D can be delivered in combination with injection of purified tumor antigen protein, tumor antigen expressed from injected DNA, or tumor antigen peptides that are presented to effector cells using dendritic cell-based therapies. Examples of these types of therapies include the use of cytokines like IL-2 in the context of vaccination with modified tumor cells (Antonia S J et al., J. Urol. 167:1995-2000, 2002; and Schrayer D P et al., Clin. Exp. Metastasis 19:43-53, 2002), DNA (Niethammer A G et al., Cancer Res. 61:6178-84, 2001), and dendritic cells (Shimizu K et al., Proc. Nat. Acad. Sci. USA 96:2268-73, 1999). Similarly, IL-17D can be used as an anti-cancer vaccine adjuvant.

IL-17D can be used in the context of gene therapy. Gene therapy can be broadly defined as the transfer of genetic material into a cell to transiently or permanently alter the cellular phenotype. Numerous methods are being developed for delivery of cytokines, tumor antigens, and additional co-stimulatory molecules via gene therapy to specific locations within tumor patients (reviewed in Rosenberg, S A ibid). These methodologies could be adapted to use IL-17D DNA or RNA, or IL-17D could be used as a protein adjuvant to enhance immunity in combination with a gene therapy approach as described herein.

Gene therapy for cancer by the introduction of nucleic acid molecules encoding cytokines is based on the concept of enhancing the immune response against the tumor cells. The ultimate goal of this approach is to obtain regression of the treated tumor and simultaneously induce such a high degree of immunity that coexisting metastases are also destroyed. The mechanism by which the cytokine enhances the immune response against the tumor cells most likely in many cases involves eliciting an inflammatory type cell infiltration that results in improved antigen presentation. During the local inflammation, invading cells may lyse the tumor cells, releasing tumor antigens in a form that can be presented by other subpopulations of the invaders to T lymphocytes. These, in their turn, could act against coexisting metastases. Compared to administration of a cytokine protein, the gene transfer approach has the important advantage of high-level production of the cytokine at the site of the tumor, while systemic concentrations of the cytokine remain low. This avoids any pleiotropic and toxic side effects associated with cytokine Successful cancer treatment have been obtained with tumor cells expressing interleukin 2 (IL-2) (Fearon et al., Cell 60:397-401, 1990); Gansbacher et al., J. Exp. Med. 172:1217, 1990), IL-4 (Golumbek et al., Science 254:713-716, 1991; Platzer et al., Eur. J. Immunol. 22:1729-1733, 1992), interferon-gamma (Gansbacher et al., Cancer Res. 50:7820-7824, 1990), interferon-alpha (Ferrantini et al., Cancer Res. 53:1107-1112, 1993), TNF alpha (Blankenstein et al., J. Exp. Med. 173:1047-1052, 1991), IL-7 (Hock et al., J. Exp. Med. 174:1291-1298,1991; McBride et al., Cancer Res. 52:3931-3937, 1992), G-CSF (Colombo et al., J. Exp. Med. 173:889-897, 1991), GM-CSF (Dranoff et al., Proc. Natl. Acad. Sci. U.S.A. 90:3539-3543, 1993), IL-12 (Tahara et al., Cancer Res. 54:182-189, 1994), IL-1 (Apte et al., In: Cytokine-induced tumor immunogenicity, Acad. Press London, pp. 97-112, 1994; Apte et al., Folia Biol. Praha 40:1-18, 1994; Douvdevani et al, Int. J. Cancer 51:822-830, 1992; Nakata et al., Cancer Res. 48:584-588,1988; Zoller et al., Int. J. Cancer 50:443-449, 1992) and IL-3 (McBride et al., Folia Biol. Praha 40:62-73, 1993; Pulaski et al., Cancer Res. 53:2112-2117, 1993). Partial regression of a nonimmunogenic solid tumor subcutaneously implanted in WAG/Rij rats has been observed after intratumor injection of adenoviral vectors expressing IL-1a or IL-3 (L42 nonsmall cell lung cancer; Kal et al., NCI Monographs 6:111-114,1988; Kal et al., Radiother. Oncol. 6:231-238, 1986; Kal et al., J. Natl. Cancer Inst. 76:943-946, 1986). This regression occurred both in the injected tumor and in an untreated distant (contralateral) L42 tumor (patent application EP 96.202725).

Accordingly, genetically modified cells (e.g., non-cancerous cells, solid tumor cells and cells of the vasculature of a solid tumor) expressing the interleukin-17D in the body of a mammal find use in the treatment and prevention of cancers. The expression of interleukin-17D in transduced cells (e.g., non-cancerous cells, solid tumor cells or cells of the vasculature of a solid tumor) results in an effective killing of the cells. Thus, the present invention also provides a gene therapy treatment for solid tumors. The proliferation or growth of tumors that are in close contact with the circulation, e.g., vascularized solid tumors, can be inhibited or reduced by systemic administration of a viral vector encoding a polynucleotide expressing IL-17D. Examples of types of solid tumors include, but are not limited to, carcinomas (e.g., of the lung, bladder, kidney, breast, stomach, pancreas, urogenital tract, and intestine), sarcomas (e.g., soft tissue sarcomas, osteogenic sarcomas, or Kaposi's sarcoma), gliomas and melanomas. Also benign types of tumors, such as, e.g., angiomas and fibrocytomas, can be treated according to the invention. In various embodiments, non-cancerous cells of the same tissue type as the cancer are transduced with a nucleic acid encoding IL-17D and administered to the subject.

b. Routes of Administration

IL-17D can be formulated into pharmaceutical formulations for administration to a patient. Administration of the pharmaceutical formulations can be by a variety of methods. Methods can include systemic administration, wherein the IL-17D polypeptide is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration, with the proviso that, as used herein, systemic administration does not include direct administration to the brain region by means other than via the circulatory system, such as intrathecal injection and intracranial administration. In other embodiments administration of the Il-17D is local, e.g., topically or intratumorally.

In some embodiments, the IL-17D is delivered in a viral vector, e.g., in a retroviral vector (e.g., in a lentiviral) or adenoviral vector. There are several ways to administer recombinant viral vectors with therapeutic genes into solid tumors that grow in a mammalian animal body. Cancer gene therapy protocols have used direct injection of the recombinant vector into the tumor (e.g., Haddada et al., Biochem. Biophys. Res. Comm. 195:1174-1183, 1993; Vincent et al., Hum. Gene Ther. 7:197-205, 1996). However, metastases, and micrometastases, e.g., in advanced cancer, are difficult to reach with this approach. Therefore, such a gene therapy relies on a distant (immune mediated) effect of the introduced genetic information. The distant effect may not be complete.

The viral vector can also be administered via the blood or lymphatic circulation. Established tumors, both primary and metastatized, that are larger than a few millimeters in diameter are vascularized (Folkman et al., J. Nat. Cancer Inst. 82:4, 1990; Folkman and Shing, J. Biol. Chem. 267:10931-10934, 1992). In addition, distant metastases usually emerge after migration of tumor cells from the primary tumor through the blood or lymphatic circulation. Thus, solid tumors are in close contact with the circulation can be reached via the circulation.

In some embodiments, the IL-17D is delivered in cells (e.g., non-cancerous or tumor cells) transduced with an IL-17D polynucleotide to recombinantly express IL-17D. Transduced cells (e.g., non-cancerous and tumor cells) can be injected directly into a tumor or administered via the circulatory system, e.g., intravenously.

c. Dosing

The IL-17D can be administered for prophylactic and/or therapeutic treatments. In therapeutic applications, compositions comprising the IL-17D are administered to a patient suffering from a disease or malignant condition, such as cancer, in an amount sufficient to cure or at least partially arrest the disease and its complications. An amount adequate to accomplish this is defined as a "therapeutically effective dose." Amounts effective for this use will depend upon the severity of the disease and the general state of the patient's health, and clinical studies are often done to determine the best dose for a given cancer type. An effective amount of the compound is that which provides either subjective relief of a symptom(s) or an objectively identifiable improvement as noted by the clinician or other qualified observer.

In prophylactic applications, compositions containing the IL-17D is administered to a patient not already in a disease state to prevent the onset of disease. Such an amount is defined to be a "prophylactically effective dose." In this use, the precise amounts again depend upon the patient's state of health.

Determination of an effective amount is well within the capability of those skilled in the art, especially in light of the detailed disclosure provided herein. Generally, an efficacious or effective amount of IL-17D is determined by first administering a low dose or small amount of a polypeptide or composition and then incrementally increasing the administered dose or dosages, adding a second or third medication as needed, until a desired effect is observed in the treated subject with minimal or no toxic side effects. Applicable methods for determining an appropriate dose and dosing schedule for administration of a combination of the present invention are described, for example, in Goodman and Gilman's The Pharmacological Basis of Therapeutics, 11 th Edition, 2006, supra; in a Physicians' Desk Reference (PDR), 64th Edition, 2010; in Remington: The Science and Practice of Pharmacy, 21st Ed., 2006, supra; and in Martindale: The Complete Drug Reference, Sweetman, 2005, London: Pharmaceutical Press., and in Martindale, Martindale: The Extra Pharmacopoeia, 31st Edition, 1996, Amer Pharmaceutical Assn, each of which are hereby incorporated herein by reference.

Exemplary doses of the pharmaceutical formulations described herein, include nanogram or microgram amounts per kilogram of subject or sample weight (e.g., about 1 nanogram per-kilogram to about 500 micrograms per kilogram, about 10 nanograms per kilogram to about 50 micrograms per kilogram, or about 100 nanograms per kilogram to about 5 micrograms per kilogram. It is furthermore understood that appropriate doses of IL-17D polypeptides or polynucleotides depend upon the potency of the composition with respect to the desired effect to be achieved. When the IL-17D is to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

The appropriate dosage of IL-17D will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

The dosage of IL-17D administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular compound in a particular subject. A unit dosage for administration to a mammal of about 50 to 70 kg may contain between about 5 and 500 mg of the active ingredient. Typically, a dosage of the IL-17D is a dosage that is sufficient to achieve the desired effect.

Optimum dosages, toxicity, and therapeutic efficacy of compositions can further vary depending on the relative potency of individual compositions and can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, LD50/ED50. Compositions that exhibit large therapeutic indices are preferred. While compositions that exhibit toxic side effects can be used, care should be taken to design a delivery system that targets such compositions to the site of affected tissue to minimize potential damage to normal cells and, thereby, reduce side effects.

The data obtained from, for example, animal studies (e.g., rodents and monkeys) can be used to formulate a dosage range for use in humans. The dosage of polypeptides of the present invention lies preferably within a range of circulating concentrations that include the ED50 with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the IC50 (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a polypeptide or composition, is from about 1 ng/kg to 500 mg/kg for a typical subject.

A typical polypeptide composition of the present invention for intravenous administration would be about 0.1 to 10 mg/kg per patient per day. Dosages from 0.1 up to about 100 mg/kg per patient per day may be used. Actual methods for preparing administrable compositions will be known or apparent to those skilled in the art and are described in more detail in such publications as Remington: The Science and Practice of Pharmacy, 21st Ed., 2006, Lippincott Williams & Wilkins.

In one embodiment of the present invention, a pharmaceutical formulation of the present invention is administered, e.g., in a daily dose in the range from about 1 mg of compound per kg of subject weight (1 mg/kg) to about 1 g/kg. In another embodiment, the dose is a dose in the range of about 5 mg/kg to about 500 mg/kg. In yet another embodiment, the dose is about 10 mg/kg to about 250 mg/kg. In another embodiment, the dose is about 25 mg/kg to about 150 mg/kg.

In embodiments where IL-17D is delivered in the form of a polynucleotide, typical dosages can range from about 0.1 mg/kg body weight up to and including about 100 mg/kg body weight, for example, between about 1 mg/kg body weight to about 50 mg/kg body weight. In some embodiments, the dose of nucleic acid is about 1.5, 2, 3, 4, 5, 10, 15, 20, 30, 40 or 50 mg/kg body weight.

In embodiments where the IL-17D is delivered in a viral vector, the viral vector is delivered at the dosage that retains sufficient stability of the infectivity of the viral vector for a time long enough to allow uptake of the vector into the solid tumor cells and/or endothelial cells of the vasculature of a solid tumor after administration of the composition to the circulation of the recipient mammal. Typically, a pharmaceutical composition comprising one dose contains at least about $1 \times 10^6$, preferably about $1 \times 10^8$ infectious units (i.u.) of the adenoviral vector of the invention, but can contain at least about $1 \times 10^9$, more preferred $1 \times 10^{10}$, or even more preferred $1 \times 10^{11}$ i.u. The amount of virus to be provided depends on many parameters. Only a very limited portion of the administered virus actually infects the target cells. This may be one reason to increase the amount of virus to be administered. Also, the size of the tumor and/or the degree of its vascularization will influence the amount of virus required to get an effect. Another important aspect is, of course, the amount of IL-17D activity expressed by a cell infected with one or more viruses. This, of course, depends on the cell, but also on the promoter that drives the expression and its interaction with cell components of the expression machinery, etc.

Following successful treatment, it may be desirable to have the subject undergo maintenance therapy to prevent the recurrence of the disease or malignant condition treated.

d. Scheduling

Optimal dosing schedules can be calculated from measurements of polypeptides in the body of a subject. In general, dosage is from 1 ng to 500 mg per kg of body weight and may be given once or more daily, semiweekly, weekly, biweekly, semimonthly, monthly, bimonthly or yearly, as needed or appropriate. Persons of ordinary skill in the art can easily determine optimum dosages, dosing methodologies and repetition rates. One of skill in the art will be able to determine optimal dosing for administration of a polypeptide or polypeptide composition of the present invention to a human being following established protocols known in the art and the disclosure herein.

Single or multiple administrations of the pharmaceutical formulations may be administered depending on the dosage and frequency as required and tolerated by the patient. In any event, the composition should provide a sufficient quantity of the IL-17D to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

Thus, a pharmaceutical formulation thereof for intravenous administration would be about 0.01 to 100 mg/kg per patient per day. Dosages from 0.1 up to about 1000 mg/kg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as Remington: The Science and Practice of Pharmacy, 21st Ed., 2006, Lippincott Williams & Wilkins.

To achieve the desired therapeutic effect, pharmaceutical formulations may be administered for multiple days at the therapeutically effective daily dose. Thus, therapeutically effective administration of compositions to treat a disease or malignant condition described herein in a subject may require periodic (e.g., daily) administration that continues for a period ranging from three days to two weeks or longer. Typically, compositions will be administered for at least three consecutive days, often for at least five consecutive days, more often for at least ten, and sometimes for 20, 30, 40 or more consecutive days, or longer, as needed. While consecutive daily doses are a preferred route to achieve a therapeutically effective dose, a therapeutically beneficial effect can be achieved even if the compounds or compositions are not administered daily, so long as the administration is repeated frequently enough to maintain a therapeutically effective concentration of the composition in the subject. For example, one can administer a composition every other day, every third day, or, if higher dose ranges are employed and tolerated by the subject, once a week.

5. Monitoring Efficacy and Response

A variety of methods can be employed in determining efficacy of therapeutic and prophylactic treatment with the polypeptides of the present invention. Generally, efficacy is the capacity to produce an effect without significant toxicity. Efficacy indicates that the therapy provides therapeutic or prophylactic effects for a given intervention (examples of interventions can include by are not limited to administration of a pharmaceutical formulation, employment of a medical device, or employment of a surgical procedure). Efficacy can be measured by comparing treated to untreated individuals or by comparing the same individual before and after treatment. Efficacy of a treatment can be determined using a variety of methods, including pharmacological studies, diagnostic studies, predictive studies and prognostic studies. Examples of indicators of efficacy include but are not limited to inhibition of tumor cell growth and promotion of tumor cell death.

The efficacy of an anti-cancer treatment can be assessed by a variety of methods known in the art. Administration of IL-17D can be screened for prophylactic or therapeutic efficacy in animal models in comparison with untreated or placebo controls. IL-17D can be then analyzed for the capacity to induce tumor cell death or enhanced immune system activation. For example, multiple dilutions of sera can be tested on tumor cell lines in culture and standard methods for examining cell death or inhibition of cellular growth can be employed. (See, e.g., Maniatis, et al., Molecular Cloning: A Laboratory Manual, Cold Spring Harbor Lab., New York, 1982; Ausubel, et al. Editor, Current Protocols in Molecular Biology, USA, 1984-2008; and Ausubel, et al. Editor, Current Protocols in Molecular Biology, USA, 1984-2008; Bonifacino, et al., Editor, Current Protocols in Cell Biology, USA, 2010; all of which are incorporated herein by reference in their entirety.)

The methods provide for detecting inhibition of disease in patients suffering from or susceptible to various cancers. A variety of methods can be used to monitor both therapeutic treatment for symptomatic patients and prophylactic treatment for asymptomatic patients.

Monitoring methods entail determining a baseline value of a tumor burden in a patient before administering a dosage of IL-17D, and comparing this with a value for the tumor burden after treatment, respectively.

With respect to therapies using IL-17D, a significant decrease (i.e., greater than the typical margin of experimental error in repeat measurements of the same sample, expressed as one standard deviation from the mean of such measurements) in value of the tumor burden signals a positive treatment outcome (i.e., that administration of IL-17D has blocked or inhibited, or reduced progression of tumor growth and/or metastasis).

In other methods, a control value of tumor burden (e.g., a mean and standard deviation) is determined from a control population of individuals who have undergone treatment with IL-17D. Measured values of tumor burden in a patient are compared with the control value. If the measured level in a patient is not significantly different (e.g., more than one standard deviation) from the control value, treatment can be discontinued. If the tumor burden level in a patient is significantly above the control value, continued administration of agent is warranted.

In other methods, a patient who is not presently receiving treatment but has undergone a previous course of treatment is monitored for tumor burden to determine whether a resumption of treatment is required. The measured value of tumor burden in the patient can be compared with a value of tumor burden previously achieved in the patient after a previous course of treatment. A significant decrease in tumor burden relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant increase in tumor burden relative to the control level (i.e., more than a standard deviation) is an indicator that treatment should be resumed in a patient.

The tissue sample for analysis is typically blood, plasma, serum, mucous, tissue biopsy, tumor, ascites or cerebrospinal fluid from the patient. The sample can be analyzed for indication of neoplasia. Neoplasia or tumor burden can be detected using any method known in the art, e.g., visual observation of a biopsy by a qualified pathologist, or other visualization techniques, e.g., radiography, ultrasound, magnetic resonance imaging (MRI).

Further, the level of immune system activity in conjunction with tumor burden in a patient before administering a dosage of IL-17D can be compared this with a value for the immune system activity in conjunction with tumor burden after treatment, again respectively.

With respect to therapies involving enhanced immune system activity, a significant increase (i.e., greater than the typical margin of experimental error in repeat measurements of the same sample, expressed as one standard deviation from the mean of such measurements) in value of immune response signals a positive treatment outcome (i.e., that administration of IL-17D has achieved or augmented an immune response). Immune response signals can include but are not limited to for example assessing the enhancement of the lymphoma-specific cytotoxic effect of human peripheral blood mononuclear cells (PBMCs). If the value for the immune response signal does not change significantly, or decreases, a negative treatment outcome is indicated. In general, patients undergoing an initial course of treatment with an immunogenic agent are expected to show an increase in immune response activity with successive dosages, which eventually reaches a plateau. Administration of an agent is often continued while the immune response is increasing. Once a plateau is obtained, that is an indicator if the treatment is solely for the immune the administration of the treatment can be discontinued or reduced in dosage or frequency.

EXAMPLES

The following examples are offered to illustrate, but not to limit the claimed invention.

Example 1

IL-17D Mediates Tumor Rejection Through Recruitment of Natural Killer Cells Materials and Methods All experiments involving mice were conducted under animal protocols approved by the Washington University Animal Studies Committee and the University of California, San Diego Institutional Animal Care and Use Committee (IACUC protocol #S06201) and were in accordance with their ethical guidelines.

Cell Lines and Mice.

MCA sarcoma cell lines were generated as described (Dunn, et al., *Nature Immunol*. (2002) 3:991-998) by injecting 129/Sv mice with 1-400 µg of 3'methylcholanthrene (Sigma, St. Louis) dissolved in peanut oil, harvesting the tumor mass after it had reached >10 mm in average diameter, dissociating the mass via collagenase treatment, and culturing the cells in vitro. All experiments were done with cells passaged between 4 and 12 cycles. 129/Sv, 129/Sv RAG2−/−, C56BL/6 RAG2−/−, C56BL/6 RAG2−/−x γc−/− mice used were used for tumor transplantation experiments. Cell lines were maintained in RPMI 1640 supplemented with 10% FCS, L-glutamine, NEAA, sodium pyruvate, sodium bicarbonate, pen/strep, and β-mercaptoethanol. Daughter ctrl and sh17D regressor tumor cell lines were generated by transducing parental regressor tumor cell lines with either a retrovirus-expressing scramble sequence (shctrl) or retroviruses expressing shRNA's specific for the 3'UTR and coding sequence of IL-17D and selected on puromycin supplemented media for 1 week. Daughter ctrl and ex17D progressor tumor cell lines were generated by either transducing parental progressor tumor cell lines with an empty vector lentivirus (ctrl) or a lentivirus-expressing IL-17D cDNA and selected on blastocydin supplemented media for 1 week. Conditional expressing IL-17D daughter progressor tumor cell lines were generated by transducing parental F244 progressor tumor cell line with a lentivirus-expressing the tet repressor and selected on blastocydin for 1 week. Resulting cells were then transduced with a lentivirus-expressing IL-17D regulated by the tet operator sequence and selected on puromycin supplemented media for 1 week.

Antibodies and FACS Analysis.

All cell stains were done with 50-80% confluent cells and were repeated at least twice. Cells were harvested by trypsinization, washed once with PBS, incubated with BD CYTOFIX™ (BD biosciences, San Diego Calif.) for 15 min at 4° C., washed twice with BD PERM/WASH™ (BD biosciences, San Diego Calif.) solution, and anti-IL17D (R&D Systems) or rat IgG2a isotype control (eBioscience) monoclonal antibodies added. Staining was conducted for 30 minutes at 4° C. in FACS tubes containing 0.5-2 million total cells, 0.5-1 µl of antibody, and 100 µl of FACs buffer (PBS+ 1% FCS+0.09% NaN$_3$, Sigma). Cells were washed twice with Perm wash, then resuspended in FACS stain buffer. All analyses were done on live cells identified by forward and side scatter properties.

Tumor Transplantation.

Subconfluent tumor cell lines were harvested by trypsinization, washed 3× with HBSS+Ca/Mg, and injected subcutaneously into syngeneic recipient WT, RAG2−/−, or RAG2−/−x γc−/− mice at either 1×10$^6$ cells/mouse or 5×10$^6$ cells/mouse as previously described (Bui, et al., *Cancer Res* (2006) 66:7301-7309). WT mice were injected i.p. with either mouse IgG, anti-NK1.1 (PK 136), or anti-Ly6G (1A8) on days −2 and 0 and every four days post tumor transplant until tumor harvest. NK cell and neutrophil depletion was verified by FACS analysis of both spleen and tumor cell suspensions at the indicated time of harvest. For conditional expression of IL-17D in tumors in vivo, mice were administered either doxycycline (200 µg/ml) water or regular drinking water on various days post tumor transplant. Mice were monitored for tumor growth by measurement of mean tumor diameter, defined as the average of the 2 maximum dimensions of the tumor mass. On various days post-transplantation, tumors were excised from mice, minced, and treated with 1 mg/mL type IV collagenase (Sigma) as described (Bui, et al., *Cancer Res* (2006), supra). Cells were vigorously resuspended, washed in FACS buffer and filtered before staining Antibodies to CD45, CD206, CD80, CD86, CD3e, CD4, CD8, B220, CD11c, DX5, NK1.1, CD69, MAC1, K$^b$, K$^d$, I-A/I-E, and Ly6G were from eBiosciences (San Diego, Calif.).

Results

It should be noted that edited tumors possess antigens (Boon, *Int. J. Cancer* (1993) 54, 177-180; Van Der Bruggen, et al., *Immunol Rev* (2002) 188:51-64) and can even immunize the host (North, *Cancer Immunol Immunother.* (1984) 18(2):69-74; Berendt, et al., *J Exp Med.* (1980) 151(1):69-80), but the adaptive immune response to edited tumors ultimately fails, leading to cancer progression and death (Schreiber, et al., *Science* (2011) 331:1565-1570. To determine whether factors produced by unedited regressor cells can lead to rejection of edited progressor cells, we utilized a syngeneic panel of progressor and regressor MCA-induced sarcoma cell lines. We mixed a representative MCA-induced progressor sarcoma cell line (d30m1) with the MCA-induced regressor sarcoma cell lines d42m1 or d38m2 and transplanted the mixture into WT syngeneic mice. Interestingly, mixtures of progressor:regressor tumor cell lines were rejected when transplanted into WT mice (FIG. 1c), whereas the same quantity of progressor tumor cells grew in WT mice. The rejection required that the tumors were spatially and temporally localized, since mice that had rejected d42m1 regressor tumor cell lines failed to reject subsequently transplanted d30m1 progressor tumors (FIG. 5b), and placing d42m1 on the opposite flank did not lead to rejection of d30m1 (FIG. 1f). These results suggest that immune rejection of mixed progressor:regressor tumors was not associated with common antigen expression, but rather other regressor-associated molecules. While tumor-derived factors such as TGF-b9 and B7-H110 have been shown to actively suppress immune responses, it is unknown what regressor associated molecules can polarize the tumor microenvironment to promote anti-tumor immune responses.

Figure 2:
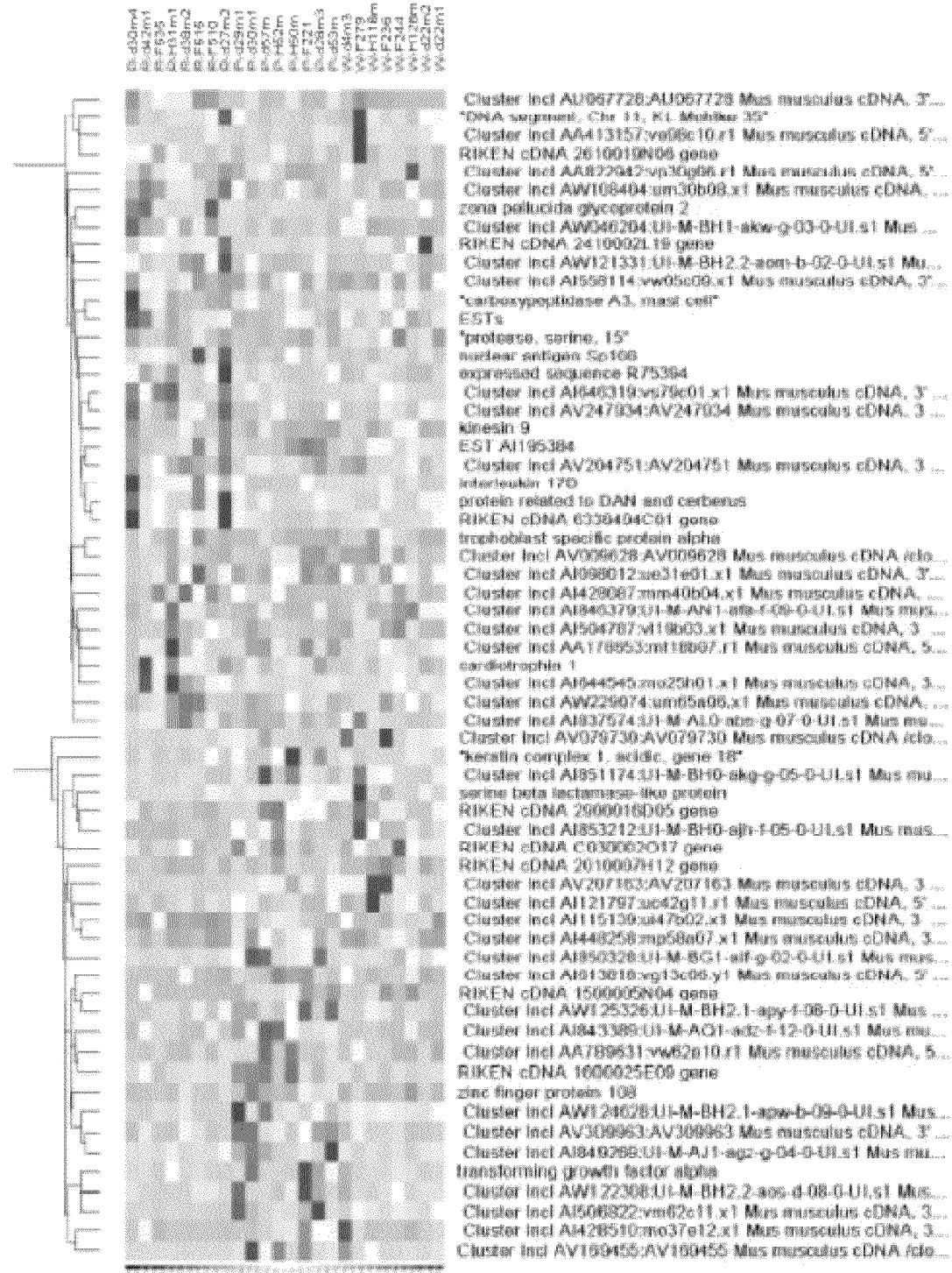
FIG. 2 illustrates that IL-17D is highly expressed in regressor tumor cell lines. Gene expression microarray clustering analysis of 8 regressor (left), 8 progressor (middle), and 8 WT progressor (right) tumor cell lines. Highly upregulated genes compared to reference are shown in dark red and highly downregulated genes are shown in dark blue.
Figure 3:
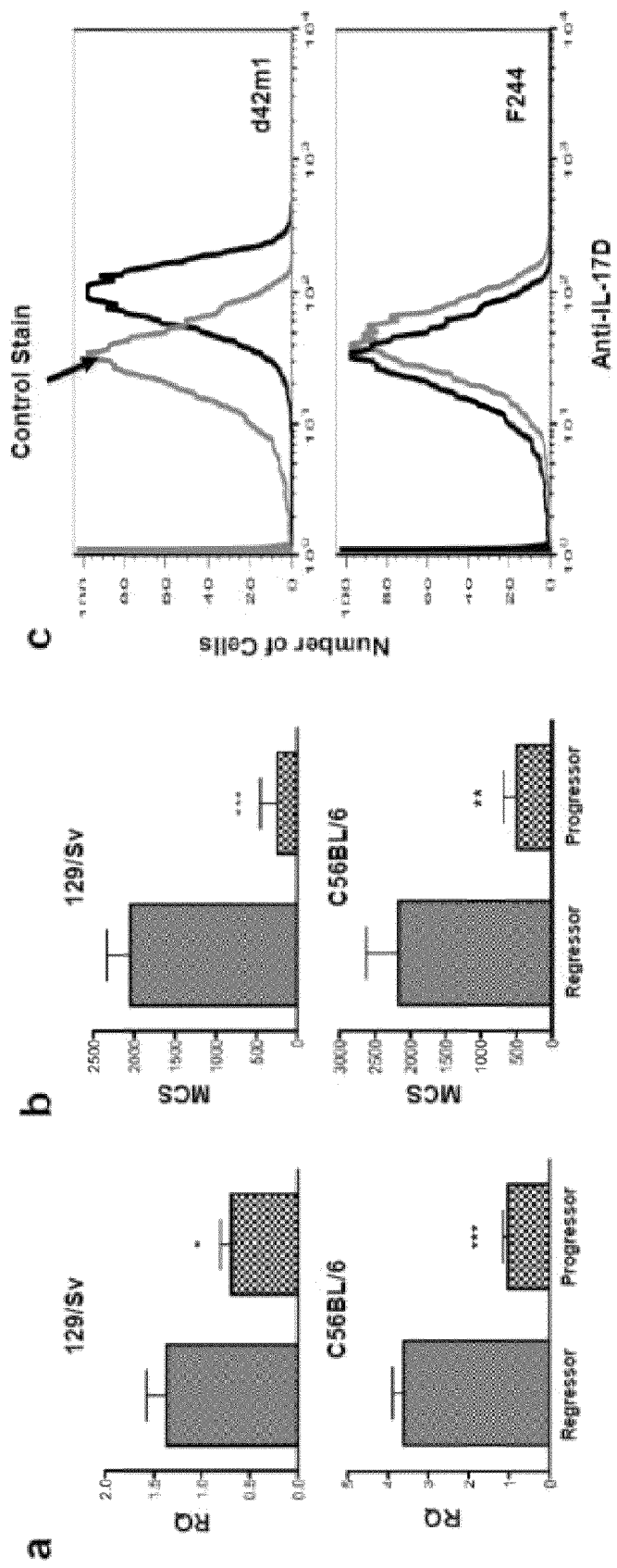
FIGS. 3A-C illustrate that IL-17D transcript and protein are highly expressed in regressor tumor cell lines. (a) qRT-PCR analysis of mRNA from 3 independent regressor and progressor tumor cell lines generated from RAG2−/− mice on the 129/Sv background (top panel), and 3 independent regressor and progressor cell lines generated from RAG2−/− x γc−/− on the C56BL/6 background (bottom panel). Values are normalized to GAPDH expression. (b) IL-17D protein levels measured by intracellular staining FACS analysis. Values are given as the mean channel shift of signal subtracted by isotype control staining as shown for a (c) representative regressor (d42m1) and progressor (F244) tumor cell lines.

To identify regressor-expressed molecules that could mediate dominant tumor rejection of progressor:regressor mixtures, we performed microarray studies of 8 independent regressor and 16 independent progressor tumor cell lines (FIG. 2). We found that cytokine IL-17D was highly upregulated in regressors compared to progressors as shown by microarray data (FIG. 1a) and confirmed by qRT-PCR (FIG. 1b, FIG. 3a) and intracellular flow cytometry (FIG. 3b-c). These results suggest that IL-17D was secreted in vitro at higher levels by regressor versus progressor tumor cell lines. Interestingly, IL-17D mRNA expression can be found in skeletal muscle and can stimulate human embryonic endothelial cells to produce IL-6, IL-8, and GM-CSF11. However, there have been no studies addressing the expression or function of IL-17D in tumor cells or any other model system.

Figure 4:
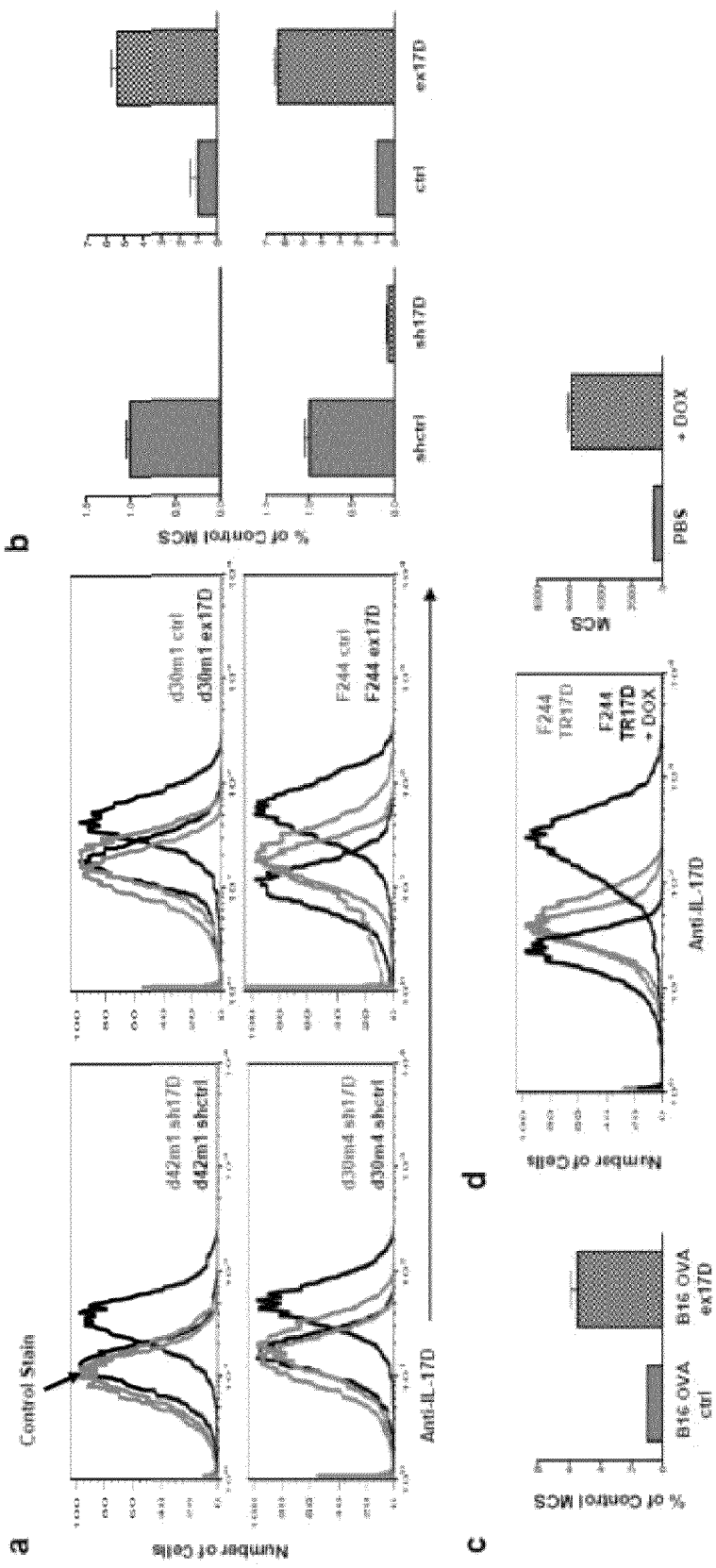
FIGS. 4A-D illustrate generation of IL-17D deficient regressor and IL-17D overexpressing progressor tumor cell lines. (a) IL-17D protein expression measured by intracellular staining FACS analysis of two regressor and progressor daughter tumor cell lines transduced with scramble control (shctrl) or IL-17D specific shRNA retrovirus (sh17D), and empty vector control (ctrl) or IL-17D cDNA lentivirus (ex17D) respectively. (b) Relative protein expression values for corresponding daughter cell lines normalized to percent of ctrl transduced cell line mean channel shift. (c) IL-17D protein expression of B16 OVA daughter cell lines transduced with either empty vector control or IL-17D cDNA lentivirus. (d) IL-17D protein expression of F244 daughter cell lines transduced with tetR and tetO IL-17D or control tetR lentivirus after 48 hour stimulation with 100 ng/ml doxycycline.
Figure 5:
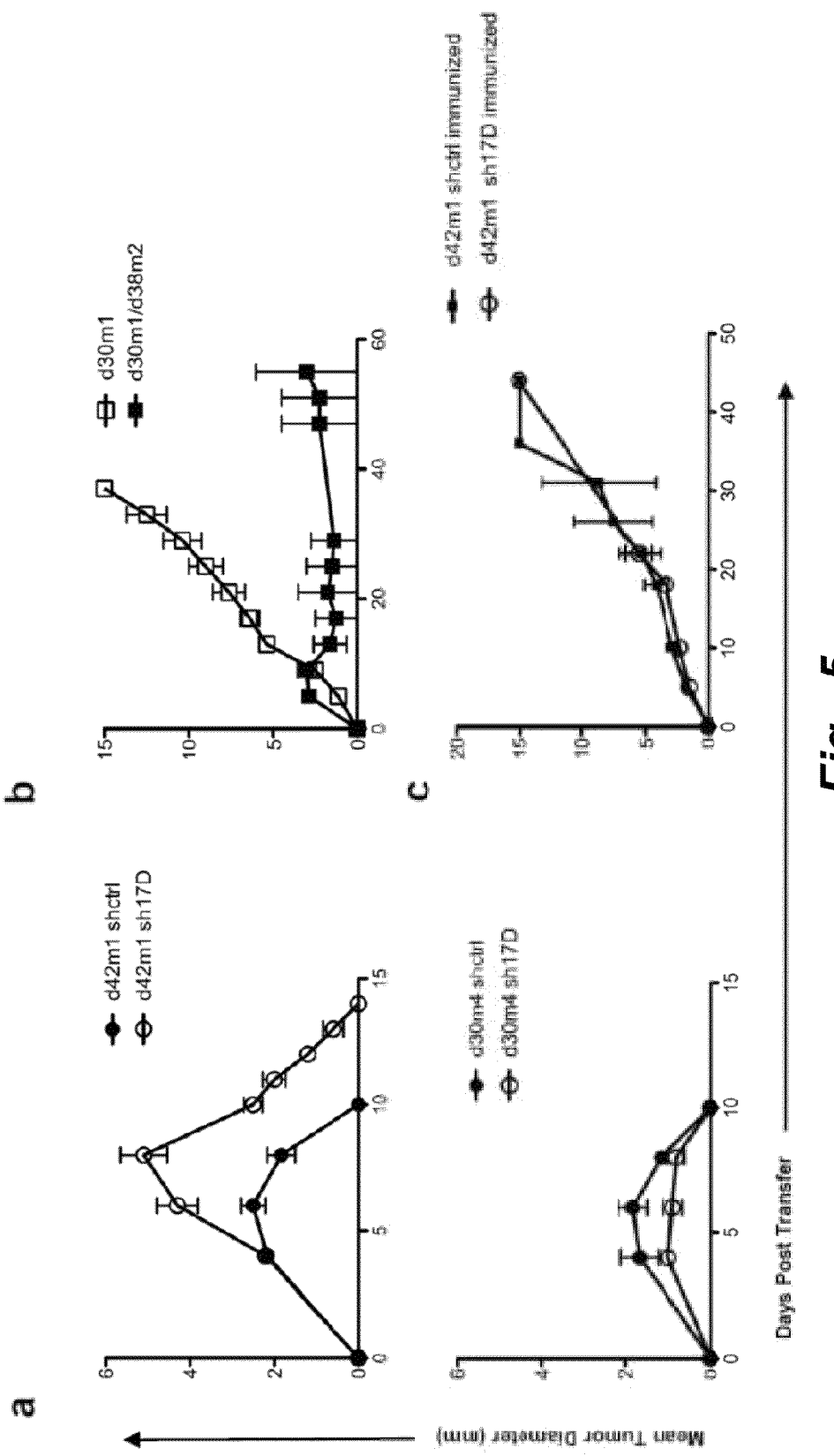
FIGS. 5A-C illustrate IL-17D is not required for the rejection of regressor tumors in WT mice. (a) d42m1 and d30m4 daughter regressor tumor cell lines were injected into WT mice and growth was measured. (b) d30m1 progressor and d38m2 tumor cell lines were mixed at a 2:1 regressor to progressor ratio and injected into WT mice. Tumor growth was measured compared to unmixed progressor control. (c) WT mice that had rejected d42m1 regressor daughter cell lines were re-challenged with d30m1 progressor tumor cell lines and tumor growth was recorded. Tumor growth was recorded as the mean of two diameter measurements of the tumor mass.
Figure 6:
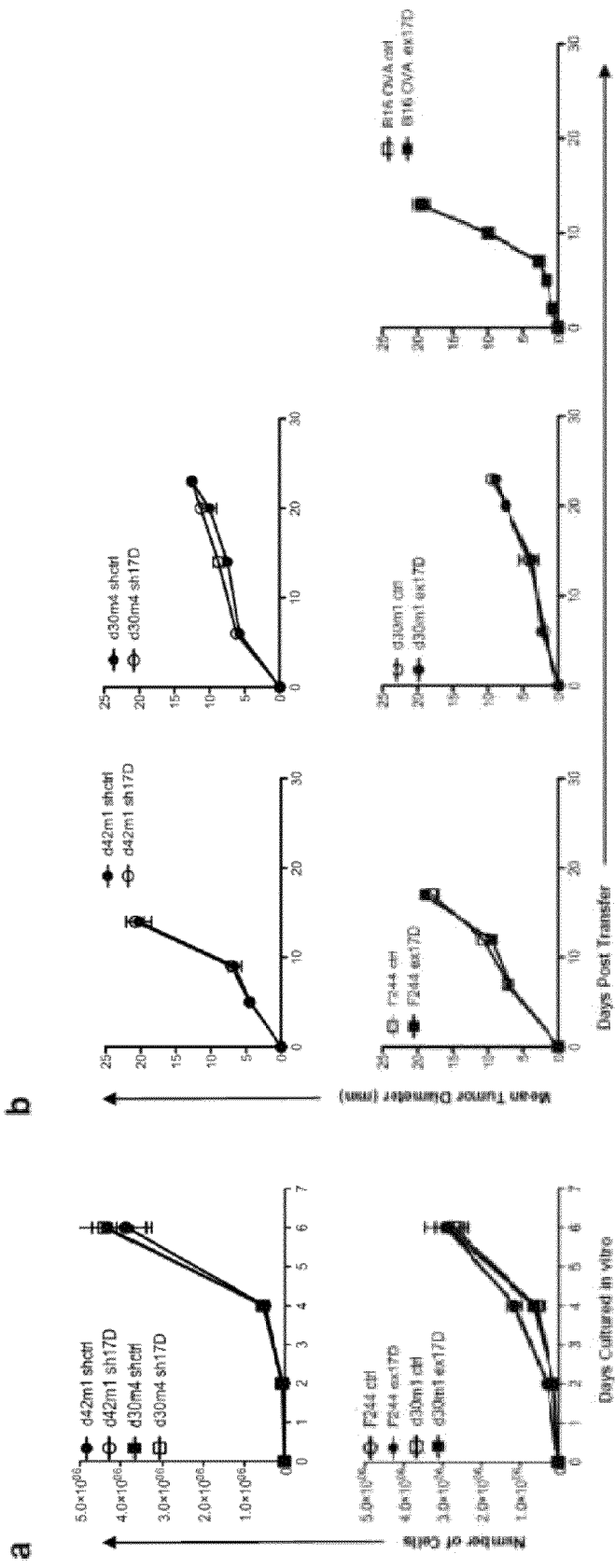
FIGS. 6A-B illustrate IL-17D expression does not influence the growth rate of tumor cells in vitro or in vivo. (a) Daughter regressor and progressor tumor cell lines were plated in vitro and viable cells were counted each day using a hemocytometer. (b) Daughter regressor and progressor tumor cell lines were injected into syngeneic RAG2−/− mice. Tumor growth was recorded as the mean of two diameter measurements of the tumor mass.

To confirm that IL-17D is required for the rejection of progressor:regressor mixtures, we silenced IL-17D in two regressor cell lines. We generated daughter cell lines transduced with scramble control (shctrl) or shRNA specific for the 3'UTR and coding regions of IL-17D (sh17D) and confirmed 90% protein knockdown (FIGS. 4a,b left panels). When the daughter cell lines were transplanted into WT mice, IL-17D knockdown did not alter the rejection phenotype (FIG. 5). Furthermore, IL-17D knockdown did not alter the in vitro growth and in vivo growth kinetics (in RAG2-/- mice) (FIGS. 6a,b) suggesting that IL-17D has no effect on intrinsic tumor growth and proliferation. We did observe, however, that IL-17D was required for the rejection of progressor:regressor mixtures, as daughter sh17D tumor cell lines mixed with d30m1 progressor tumor cell lines did not reject when transplanted into WT mice (FIG. 1c). These results suggest that a single gene (IL-17D) was required for the dominant rejection phenotype of progressor:regressor tumor mixtures.

We then explored whether IL-17D expression in progressor tumors could mediate their rejection in WT mice in the absence of other regressor-associated molecules. Two progressor fibrosarcoma and one progressor melanoma cell line (F244, d30m1, B16 OVA) were transduced with empty vector control (ctrl) or IL-17D cDNA lentivirus (ex17D), leading to approximately 5-fold overexpression of IL-17D, which is similar to regressor levels (FIGS. 4a,b,c right panels). Strikingly, the overexpression of IL-17D led to the complete rejection of both transplanted F244 and d30m1 tumors and a delay in growth of B16 OVA in WT mice (FIG. 1d). This result clearly demonstrates that early expression of IL-17D can lead to tumor rejection, but does not demonstrate the efficacy of IL-17D on pre-established tumors. In order to address this, we generated an IL-17D conditional overexpressing progressor tumor cell line (F244TR17D) that expresses IL-17D upon administration of doxycycline (FIG. 4d). Conditional expression of IL-17D was able to induce the rejection of 25 mm$^2$ tumors, but not 100 mm$^2$ tumors (FIG. 1 e), indicating that early expression of IL-17D in small tumors was critical for its rejection mechanism.

Figure 7:
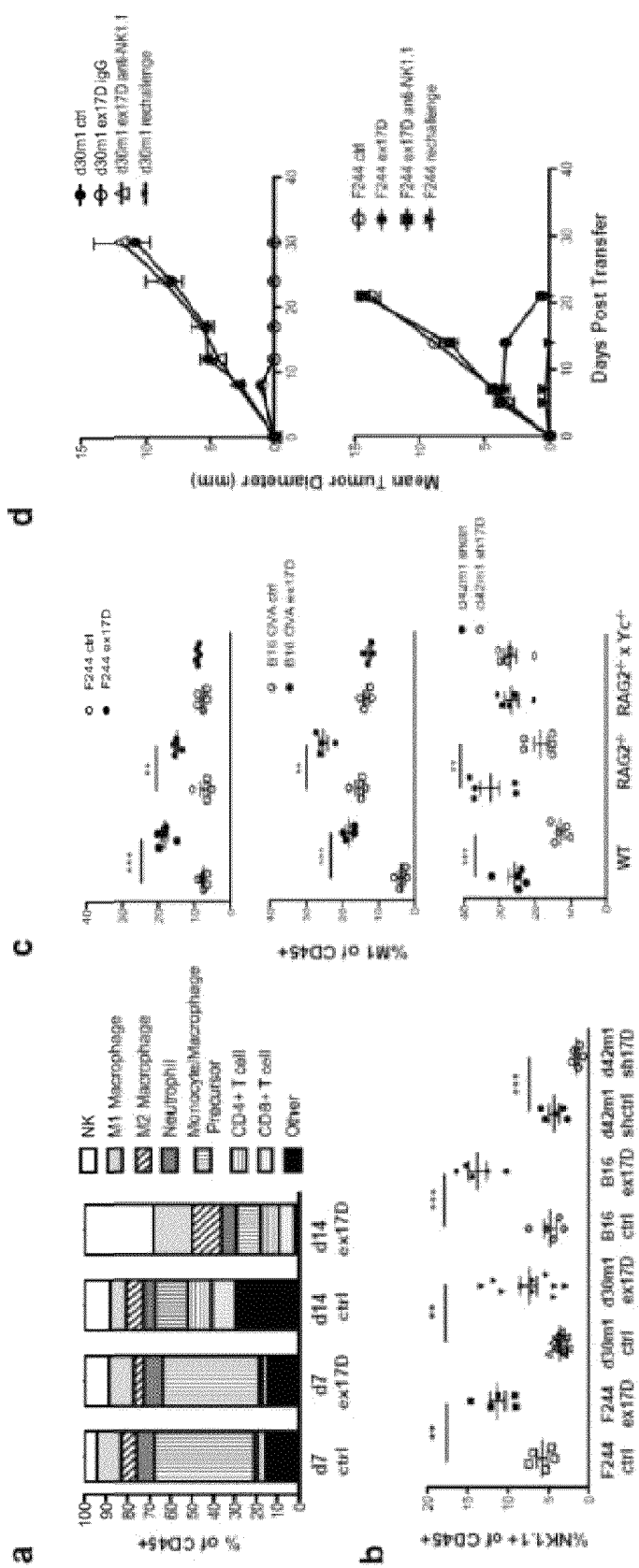
FIGS. 7A-D illustrate IL-17D overexpression leads in increased NK cells, M1 macrophage accumulation, tumor rejection, and immunological memory. (a) A progressor tumor transduced with control (ctrl) or IL-17D (ex17D) was transplanted into wild-type mice, and at day 7 or 14, the tumor mass was harvested and analyzed for immune cell infiltration by flow cytometry. (b) The percentage of NK cells was measured in control or IL-17D-expressing progressor tumors. Each symbol represents one mouse. (c) The percentage of M1 macrophages was measured in control or IL-17D-expressing progressor tumors (F244, B16ova, top two graphs) and control or IL-17D-silenced regressor tumors (d42m1, bottom graph) growing in WT, RAG2−/− or RAG2−/−x γc−/− mice. Note the failure to induce M1 macrophages in mice lacking γc, which have no NK cells. (d) NK cells are required for IL-17D-mediated rejection, which leads to memory formation. The d30m1 or F244 control or IL-17D-overexpressing cell lines were transplanted into WT mice treated with control IgG or anti-NK1.1. On the same plot is the transplantation of the parental cell line (labeled as rechallenge) into WT mice that had previously rejected the IL-17D-overexpressing cell line.

To define the mechanism of IL-17D-mediated tumor rejection, we characterized the tumor infiltrating immune cells in tumors with high and low levels of IL-17D. FACS analysis of infiltrating immune subpopulations showed an approximate 2-fold increase in the amount of CD11b-NK1.1+ cells at d7 and d14 in tumors overexpressing IL-17D compared to control tumors (FIG. 7a-b). Moreover, when IL-17D was silenced in the d42m1 regressor, there was a decrease in NK cell infiltration compared to control tumors. We also observed an approximate 1.5 fold enhancement in the accumulation of M1 macrophages in progressor tumors overexpressing IL-17D, whereas silencing of IL-17D in regressor tumors reduced M1 macrophages by approximately 2 fold in both WT and RAG2-/-, but not RAG2-/- x γc-/- hosts, which are deficient in NK cells (FIG. 7c). These results are consistent with the scenario whereby NK cells are recruited by IL-17D, leading to the generation of M1 macrophages and subsequent tumor rejection mediated by adaptive immune cells. Indeed, we have found a requirement for NK cells and IFNγ in the accumulation of M1 macrophages in regressor tumors during cancer immunoediting.

To demonstrate the functional requirement for NK cells in IL-17D-mediated tumor rejection, we depleted NK cells from WT mice transplanted with d30m1 and F244 ex17D tumors (FIG. 7d). We found that mice treated with anti-NK1.1 but not control IgG failed to reject the IL-17D-overexpressing tumors. NK-dependent tumor rejection can lead to priming of adaptive immune responses (Kelly, et al., *Nat Immunol* (2002) 3(1):83-90; Diefenbach, et al., *Nature* (2001) 413 (6852):165-171). To determine whether IL-17D-mediated rejection could prime anti-tumor immune responses, we challenged mice that had rejected IL-17D-overexpressing tumors with the parental tumor. We found that indeed transplanted parental progressor tumors were rejected after priming with IL-17D-overexpressing tumors (FIG. 7d), confirming that edited tumors possessed antigens and that initiating the "correct" innate cell response (via IL-17D) can result in productive adaptive, antigen-specific anti-tumor responses.

Figure 8:
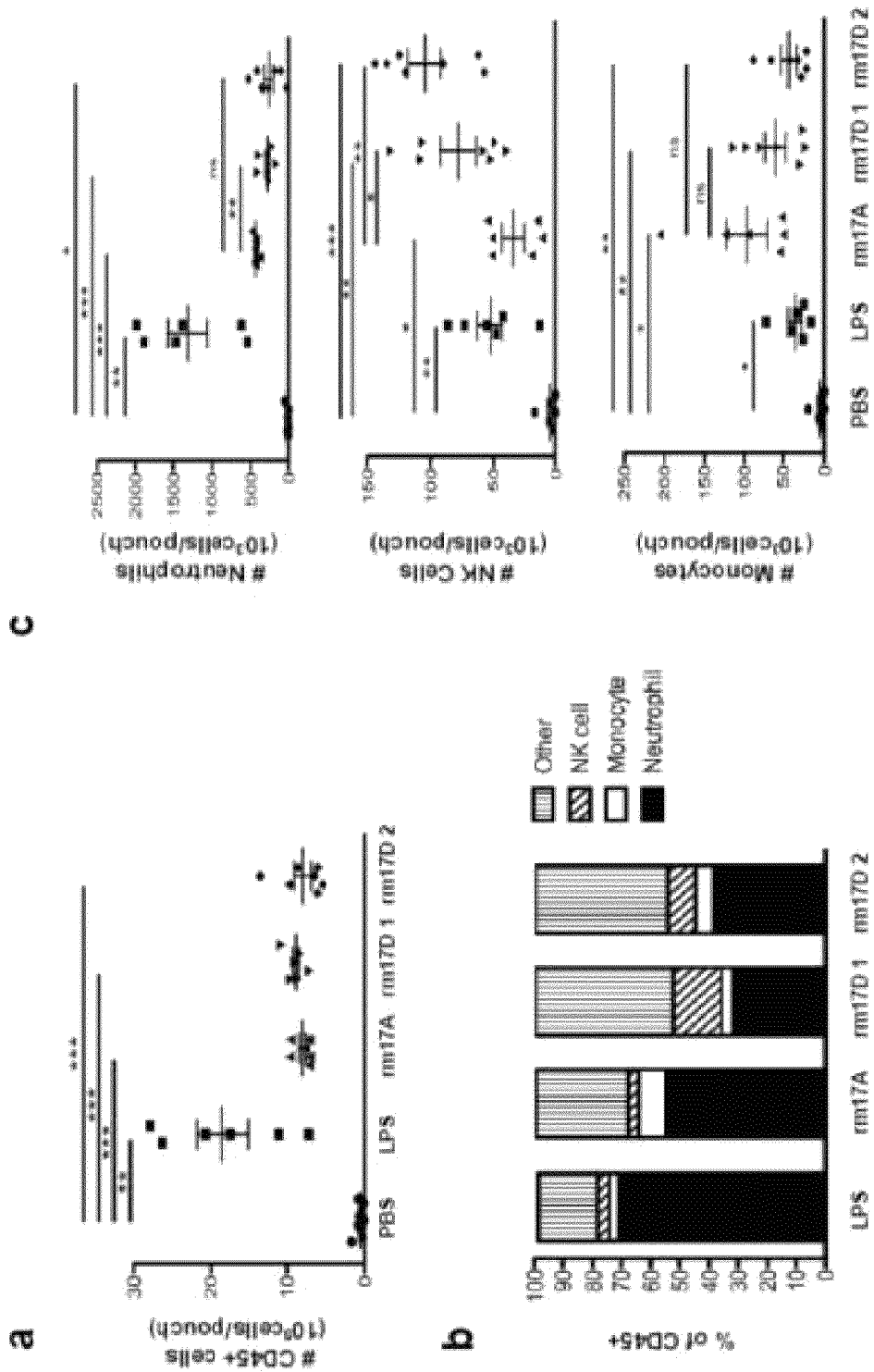
FIGS. 8A-C illustrate recombinant IL-17D recruits NK cells to a higher extent than lipopolysaccharide (LPS) and IL-17A. The indicated compound was instilled into an air pouch and eight hour later, the (a) quantity of CD45+ cells was counted and the (b) percentage and (c) number of various immune cells was measured.
Figure 9:
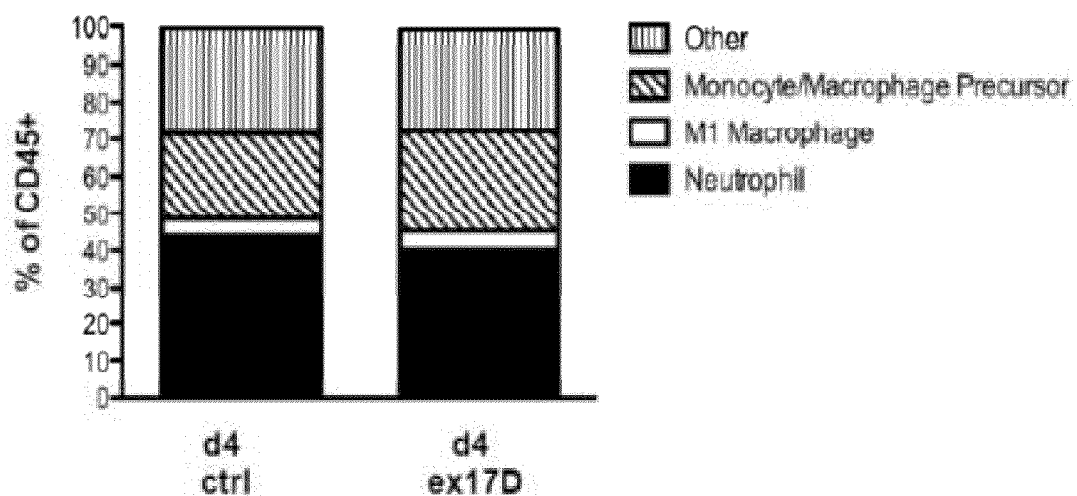
FIGS. 9A-B illustrates that overexpression of IL-17D does not recruit or require neutrophils during progressor tumor rejection. (a) F244 daughter ctrl or ex17D tumor cell lines were injected into WT mice at 5×10$^6$ cells/mouse. Tumor masses were harvested at d4, digested, and single cell suspensions were analyzed by FACS analysis ("Other" indicates tissue macrophages, T cells, B cells, and eosinophils, all of which were not differentially recruited). (b) d30m1 progressor tumor cell lines were injected into WT recipients treated with i.p. injections of ctrl IgG or ant-1A8 depleting antibodies and tumor growth was measured over time.
Figure 9:
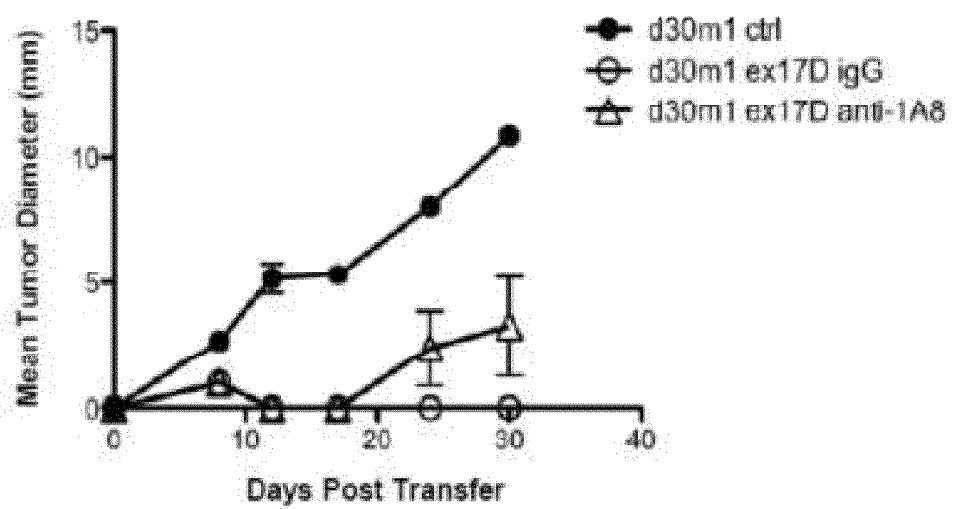

To show directly whether IL-17D can induce the recruitment of immune cells, we used an in vivo air pouch model of inflammation in WT mice. Mice injected with sterile air pouches recruit immune cells rapidly after administration of LPS 13. Indeed, we found that LPS, IL-17A, and IL-17D significantly recruited CD45+ immune cells into air pouches compared to PBS control (FIG. 8a). Whereas LPS and IL-17A recruited a larger percentage of neutrophils, IL-17D recruited a larger percentage (FIG. 8b) and number (FIG. 8c) of NK cells while also recruiting neutrophils and monocytes into air pouches. Other immune cells such as CD4+ T cells, CD8+ T cells, B cells, dendritic cells, and tissue macrophages were not differentially recruited in percentage or number and may represent the underlying inflammatory nature of the air pouch microenvironment. Although we observed recruitment of neutrophils, monocytes, and NK cells after injection of rmIL-17D into air pouches, we did not observe differential recruitment of either neutrophils or monocytes on d4 post F244 ex17D or ctrl tumor transplant (FIG. 9a). Additionally, neutrophils were not required for IL-17D mediated rejection of d30m1 progressor tumors, as mice treated with neutrophil depleting antibodies still rejected d30m1 ex17D tumors (FIG. 9b). Thus, although IL-17D can lead to the recruitment of monocytes and neutrophils in an air pouch model, IL-17D does not lead to enhanced recruitment of these cells in the context of a progressor tumor microenvironment.

Figure 10:
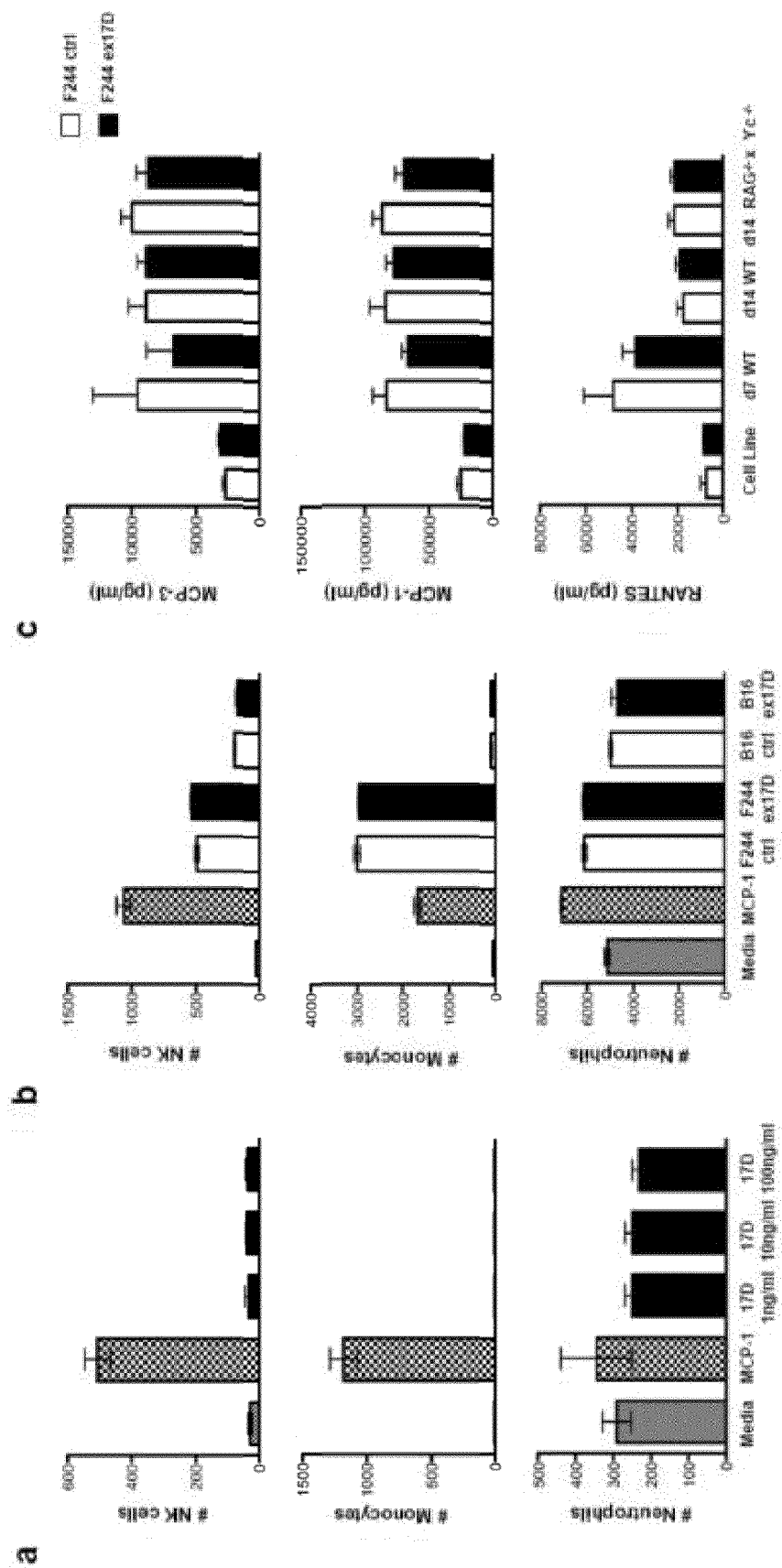
FIGS. 10A-C illustrate that IL-17D does not induce chemotaxis of immune cells in vitro. Bone marrow was harvested from WT mice and 5×10$^5$ cells were plated in the top chamber of a 5 μm transwell. Specific migration of innate cell populations was measured by FACS analysis as a response to various doses of (a) IL-17D and (b) tumor supernatant in the bottom chamber of the transwell. (c) F244 daughter cell lines were injected into WT or RAG2−/− x γc−/− hosts at 5×10$^6$ cells/mouse and tumor masses were harvested at d7 and d14. Tumors were disaggregated into single cell suspensions and plated at 4×10$^4$ cells/well in a 96 well plate for 24 hours. Supernatant was harvested and assayed for chemokine secretion levels compared to tumor cell line controls.
Figure 11:
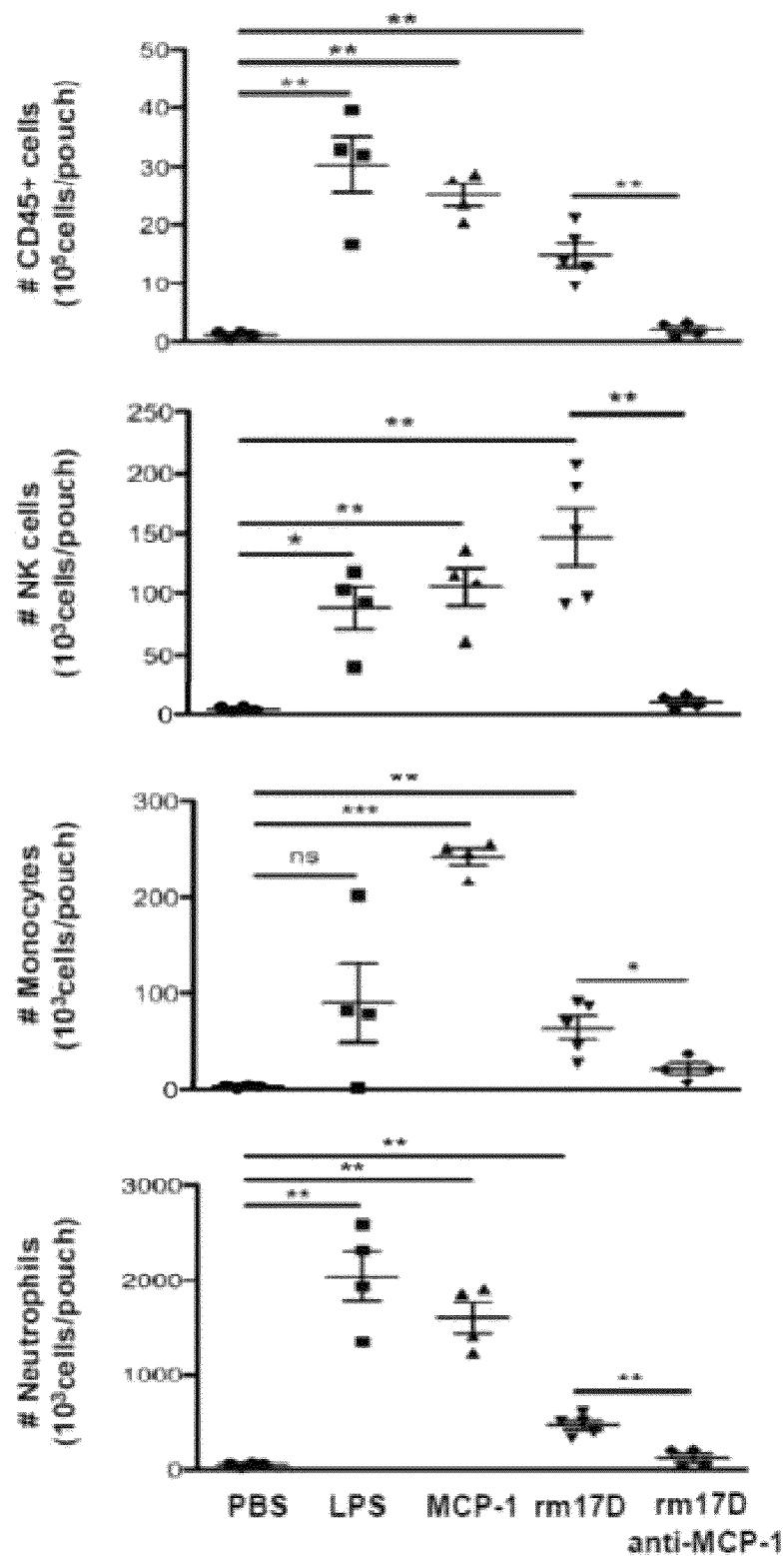
FIG. 11 illustrates that the effect of IL-17D is due to the induction of MCP-1. Recombinant IL-17D was instilled into air pouches in the presence of antibodies blocking MCP-1 activity or control antibody. Shown also are phosphate buffered saline (PBS), lipopolysaccharide (LPS), and monocyte chemoattractant protein-1 (MCP-1) controls.

We next examined whether IL-17D directly recruited NK cells or induced chemokines that could recruit NK cells. Using in vitro transwell assays, we found that IL-17D could not induce the migration of NK cells in vitro, whereas the control chemokine MCP-1 could induce robust transmigration of NK cells (FIG. 10). To determine if IL-17D induced MCP-1 to recruit NK cells in vivo, we instilled IL-17D in the presence of antibodies blocking MCP-1. We found that anti-MCP-1, but not control IgG, completely inhibited the recruitment of NK cells by IL-17D (FIG. 11). Thus, the mechanism of action of IL-17D is similar to that of IL-17A and involves the induction of chemokines to recruit innate immune cells. Interestingly, the composition of immune cells recruited by IL-17D is different from IL-17A, suggesting that these two cytokines evolved to induce specific arms of the immune response, presumably to deal with specific pathogen insults.

In summary, we advocate that the initial milieu of innate immune cells can ultimately determine whether antigenic tumors are destroyed by the immune system. We have shown that simply mixing regressor tumors with progressor tumors can lead to their rejection. Using an unbiased global expression analysis approach, we identified a single gene—IL-17D—as sufficient and necessary for the rejection of edited MCA sarcoma cell lines. We document that IL-17D can recruit NK cells via the induction of MCP-1, likely in tumor endothelial cells, leading to the generation/accumulation of M1 macrophages and priming of adaptive immune responses. Our results therefore identify a heretofore unappreciated mechanism of IL-17D in tumor surveillance and tumor rejection.

REFERENCES

1. Shankaran, V. et al. IFNc and lymphocytes prevent primary tumor development and shape tumor immunogenicity. Nature 410, 1107-1111 (2001).
2. Dunn, G. P., Bruce, A. T., Ikeda, H., Old, L. J. & Schreiber, R. D. Cancer immunoediting: from immunosurveillance to tumor escape. Nature Immunol. 3, 991-998 (2002).
3. Koebel, C. M. et al. Adaptive immunity maintains occult cancer in an equilibrium state. Nature 450, 903-907 (2007).
4. Vesely, M. D., Kershaw, M. H., Schreiber, R. D. & Smyth, M. J. Natural innate and adaptive immunity to cancer. Annu Rev. Immunol. 29, 235-271 (2011).
5. Schreiber, R. D., Old, L. J. & Smyth, M. J. Cancer immunoediting: integrating immunity's roles in cancer suppression and promotion. Science 331, 1565-1570 (2011).
6. Matsushita H. et al. Cancer exome analysis reveals a T-cell-dependent mechanism of cancer immunoediting. Nature 482, 400-404 (2012)
7. Flood, P. M., Schreiber, H. & Ron, Y. Protective immunity to progressive tumors can be induced by antigen presented on regressor tumors. J Immunol 138, 3573-3579 (1987).
8. DuPage M. et al. Expression of tumor-specific antigens underlies cancer immunoediting. Nature 482, 405-409 (2012).
9. Fridlender Z G. Et al. Polarization of tumor-associated neutrophil phenotype by TGF-beta: "N1" versus "N2" TAN. Cancer Cell 16(3), 173-174 (2009).
10. Zou W. & Chen L. Inhibitory B7-family molecules in the tumor microenvironment. Nature Reviews Immunology 8, 467-477 (2008).
11. Starnes, T., Broxmeyer, H. E., Robertson, M. J. & Hromas, R. Cutting edge: IL-17D, a novel member of the IL-17 family, stimulates cytokine production and inhibits hemopoiesis. J Immunol 169, 642-646 (2002).
12. Bui, J. D., Uppaluri, R., Hsieh, C. S. & Schreiber, R. D. Comparative analysis of regulatory and effector T cells in progressively growing versus rejecting tumors of similar origins. Cancer Res 66, 7301-7309 (2006).
13. Pelletier M. Bouchard A. & Girard D. In vivo and in vitro roles of IL-21 in inflammation. J Immunol 173, 7521-7530 (2004).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting and/or reducing the growth and/or proliferation of a cancer or cancer metastasis in a subject in need thereof comprising administering to the subject interleukin-17D (IL-17D) comprising an amino acid sequence comprising SEQ ID NO:1, wherein the IL-17D is not a component of a fusion protein, wherein the cancer is selected from the group consisting of melanoma and fibrosarcoma.

2. The method of claim 1, wherein the subject has the cancer.

3. The method of claim 1, wherein the subject is in remission from the cancer.

4. The method of claim 1, wherein the cancer expresses a tumor-associated antigen.

5. The method of claim 1, wherein the IL-17D is administered to the subject in a cell transduced to express IL-17D.

6. The method of claim 5, wherein the cell is a non-cancerous cell.

7. The method of claim 5, wherein the cell is a tumor cell.

8. The method of claim 7, wherein the tumor cell transduced to express IL-17D is a regressor tumor cell.

9. The method of claim 1, wherein the IL-17D is administered to the subject as a polypolypeptide.

10. The method of claim 9, wherein the IL-17D polypeptide is administered intravenously.

11. The method of claim 9, wherein the IL-17D polypeptide is administered intratumorally.

12. A method of inhibiting or reducing the growth and/or proliferation of a cancer cell, wherein the cancer cell is selected from a melanoma cell and a fibrosarcoma cell, comprising contacting the cancer cell with interleukin-17D (IL-17D) comprising an amino acid comprising SEQ ID NO: 1, wherein the IL-17D is not a component of a fusion protein.

* * * * *

SEQUENCE LISTING

```
<160> NUMBER OF SEQ ID NOS: 2

<210> SEQ ID NO 1
<211> LENGTH: 202
<212> TYPE: PRT
<213> ORGANISM: Homo sapiens

<400> SEQUENCE: 1

Met Leu Val Ala Gly Phe Leu Leu Ala Leu Pro Pro Ser Trp Ala Ala
1               5                   10                  15

Gly Ala Pro Arg Ala Gly Arg Arg Pro Ala Arg Pro Arg Gly Cys Ala
            20                  25                  30

Asp Arg Pro Glu Glu Leu Leu Glu Gln Leu Tyr Gly Arg Leu Ala Ala
        35                  40                  45

Gly Val Leu Ser Ala Phe His His Thr Leu Gln Leu Gly Pro Arg Glu
```

```
                    50                  55                  60
Gln Ala Arg Asn Ala Ser Cys Pro Ala Gly Gly Arg Pro Ala Asp Arg
 65                  70                  75                  80

Arg Phe Arg Pro Pro Thr Asn Leu Arg Ser Val Ser Pro Trp Ala Tyr
                 85                  90                  95

Arg Ile Ser Tyr Asp Pro Ala Arg Tyr Pro Arg Tyr Leu Pro Glu Ala
                100                 105                 110

Tyr Cys Leu Cys Arg Gly Cys Leu Thr Gly Leu Phe Gly Glu Glu Asp
                115                 120                 125

Val Arg Phe Arg Ser Ala Pro Val Tyr Met Pro Thr Val Val Leu Arg
            130                 135                 140

Arg Thr Pro Ala Cys Ala Gly Gly Arg Ser Val Tyr Thr Glu Ala Tyr
145                 150                 155                 160

Val Thr Ile Pro Val Gly Cys Thr Cys Val Pro Glu Pro Glu Lys Asp
                165                 170                 175

Ala Asp Ser Ile Asn Ser Ser Ile Asp Lys Gln Gly Ala Lys Leu Leu
            180                 185                 190

Leu Gly Pro Asn Asp Ala Pro Ala Gly Pro
        195                 200
```

<210> SEQ ID NO 2
<211> LENGTH: 1873
<212> TYPE: DNA
<213> ORGANISM: Homo sapiens

<400> SEQUENCE: 2

```
aaaatgttttt cagctcctgg aggcgaaagg tgcagagtcg ctctgtgtcc gtgaggccgg    60
gcggcgacct cgctcagtcg gcttctcggt ccgagtcccc gggtctggat gctggtagcc   120
ggcttcctgc tggcgctgcc gccgagctgg gccgcgggcg cccgagggc gggcaggcgc    180 cccgcgcggc cgcggggctg cgcggaccgg ccggaggagc tactggagca gctgtacggg   240
cgcctggcgg ccggcgtgct cagtgccttc caccacacgc tgcagctggg gccgcgtgag   300
caggcgcgca acgcgagctg cccggcaggg ggcaggcccg ccgaccgccg cttccggccg   360
cccaccaacc tgcgcagcgt gtcgccctgg gcctacagaa tctcctacga cccggcgagg   420 tacccccaggt acctgcctga agcctactgc ctgtgccggg gctgcctgac cgggctgttc   480
ggcgaggagg acgtgcgctt ccgcagcgcc cctgtctaca tgcccaccgt cgtcctgcgc   540
cgcacccccg cctgcgccgg cggccgttcc gtctacaccg aggcctacgt caccatcccc   600
gtgggctgca cctgcgtccc cgagccggag aaggacgcag acagcatcaa ctccagcatc   660
gacaaacagg gcgccaagct cctgctgggc ccaacgacg cgcccgctgg cccctgaggc    720
cggtcctgcc ccgggaggtc tccccggcc gcatcccgag gcgcccaagc tggagccgcc   780
tggagggctc ggtcggcgac ctctgaagag agtgcaccga gcaaaccaag tgccggagca   840
ccagcgccgc ctttccatgg agactcgtaa gcagcttcat ctgacacggg catccctggc   900
ttgcttttag ctacaagcaa gcagcgtggc tggaagctga tgggaaacga cccggcacgg   960
gcatcctgtg tgcggcccgc atggagggtt tggaaaagtt cacggaggct ccctgaggag  1020
cctctcagat cggctgctgc gggtgcaggg cgtgactcac cgctgggtgc ttgccaagaa  1080
gatagggacg catatgcttt ttaaagcaat ctaaaaataa taataagtat agcgactata  1140
tacctacttt taaatcaac tgttttgaat agaggcagag ctattttata ttatcaaatg  1200
agagctactc tgttacattt cttaacatat aaacatcgtt ttttacttct tctggtagaa  1260
```

-continued

```
tttttttaaag cataattgga atccttggat aaattttgta gctggtacac tctggcctgg    1320
gtctctgaat tcagcctgtc accgatggct gactgatgaa atggacacgt ctcatctgac    1380
ccactcttcc ttccactgaa ggtcttcacg ggcctccagg tggaccaaag ggatgcacag    1440
gcggctcgca tgccccaggg ccagctaaga gttccaaaga tctcagattt ggttttagtc    1500
atgaatacat aaacagtctc aaactcgcac aattttttcc ccctttgaa agccactggg     1560 gccaatttgt ggttaagagg tggtgagata agaagtggaa cgtgacatct ttgccagttg    1620
tcagaagaat ccaagcaggt attggcttag ttgtaagggc tttaggatca ggctgaatat    1680
gaggacaaag tgggccacgt tagcatctgc agagatcaat ctggaggctt ctgtttctgc    1740
attctgccac gagagctagg tccttgatct tttctttaga ttgaaagtct gtctctgaac    1800
acaattattt gtaaaagtta gtagttcttt tttaaatcat taaaagaggc ttgctgaagg    1860
aaaaaaaaaa aaa                                                        1873
```